(12) United States Patent
Dorward et al.

(10) Patent No.: US 11,045,294 B2
(45) Date of Patent: Jun. 29, 2021

(54) ORAL CARE CLEANING SYSTEM UTILIZING ENTRAINED FLUID

(71) Applicant: Johnson & Johnson Consumer Inc., Skillman, NJ (US)

(72) Inventors: Brian Dorward, Great Meadows, NJ (US); Tara Fourre, Clark, NJ (US); Justin McDonough, Flemington, NJ (US); Davide Miksa, Doylestown, PA (US); Jin Seo, Summit, NJ (US); Deepak Sharma, Flemington, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/611,057

(22) Filed: Jun. 1, 2017

(65) Prior Publication Data
US 2018/0344441 A1   Dec. 6, 2018

(51) Int. Cl.
| | |
|---|---|
| *A61C 17/02* | (2006.01) |
| *A61C 17/028* | (2006.01) |
| *A61C 1/00* | (2006.01) |
| *A61C 17/022* | (2006.01) |
| *A61K 8/34* | (2006.01) |
| *A61Q 11/00* | (2006.01) |

(52) U.S. Cl.
CPC ........ *A61C 17/0217* (2013.01); *A61C 1/0015* (2013.01); *A61C 1/0092* (2013.01); *A61C 17/022* (2013.01); *A61C 17/028* (2013.01); *A61C 17/0211* (2013.01); *A61K 8/34* (2013.01); *A61Q 11/00* (2013.01); *A61K 2800/30* (2013.01)

(58) Field of Classification Search
CPC ... A61C 17/02; A61C 17/0211; A61C 17/028; A61C 17/0217; A61C 17/022; A61C 1/0092; A61C 1/0015; A61H 13/005
USPC ...... 601/162–165; 137/119.01, 119.1, 627.5, 137/826, 830, 832
See application file for complete search history.

(56) References Cited

U.S. PATENT DOCUMENTS

| | | |
|---|---|---|
| 3,379,192 A | 4/1968 | Warren, Jr. |
| 4,051,234 A | 9/1977 | Gieske et al. |
| 4,164,940 A | 8/1979 | Quinby |
| 5,190,747 A | 3/1993 | Sekiguchi et al. |
| 5,328,682 A | 7/1994 | Pullen et al. |
| 7,084,104 B2 | 8/2006 | Martin et al. |

(Continued)

FOREIGN PATENT DOCUMENTS

| | | |
|---|---|---|
| CN | 104010588 A | 8/2014 |
| EP | 2749247 A2 | 7/2014 |
| JP | 2015009046 A | 1/2015 |

OTHER PUBLICATIONS

International Search Report; PCT/IB2018/053448 dated Aug. 9, 2018.

*Primary Examiner* — Edward Moran

(57) ABSTRACT

The present invention provides for oral care systems comprising: an appliance comprising a first and second plurality of nozzles, the appliance configured to be held in the mouth of a user with the first and second plurality of nozzles in fluid communication with one or more surfaces of the user's oral cavity; a source of gas; a source of liquid; and a fluid controller for directing entrained fluid to the appliance. Also provided are methods of cleaning, or otherwise providing benefits to, one or more surfaces of the oral cavity using a system of the present invention.

12 Claims, 8 Drawing Sheets

(56) References Cited

U.S. PATENT DOCUMENTS

| | | |
|---|---|---|
| 7,087,650 B2 | 8/2006 | Lennon |
| 7,417,020 B2 | 8/2008 | Fevola et al. |
| 9,011,416 B2 * | 4/2015 | Monty ................ A61C 1/0069 |
| | | 606/2 |
| 9,504,542 B2 | 11/2016 | DeGentile |
| 10,860,770 B2 | 12/2020 | Chang et al. |
| 2010/0167236 A1 | 7/2010 | Edwards et al. |
| 2011/0027746 A1 | 2/2011 | McDonough et al. |
| 2011/0027747 A1 | 2/2011 | Fougere et al. |
| 2012/0021375 A1 * | 1/2012 | Binner ................... A61B 5/097 |
| | | 433/89 |
| 2012/0077143 A1 | 3/2012 | Fougere et al. |
| 2012/0107765 A1 * | 5/2012 | Kloster .............. A61C 17/0202 |
| | | 433/89 |
| 2012/0189976 A1 | 7/2012 | McDonough et al. |
| 2013/0323676 A1 | 12/2013 | Abdala Pastor |
| 2016/0022395 A1 * | 1/2016 | Chang ................ A61C 17/0202 |
| | | 433/82 |
| 2016/0270889 A1 | 9/2016 | Casabonne |
| 2017/0056143 A1 | 3/2017 | Hyun |

\* cited by examiner

ORAL CARE CLEANING SYSTEM UTILIZING ENTRAINED FLUID

FIELD OF THE INVENTION

The present invention relates to oral care systems suitable for in-home use to provide a beneficial effect to the oral cavity of a mammal.

BACKGROUND OF THE INVENTION

In addition to regular professional dental checkups, daily oral hygiene is generally recognized as an effective preventative measure against the onset, development, and/or exacerbation of periodontal disease, gingivitis and/or tooth decay. Unfortunately, however, even the most meticulous individuals dedicated to thorough brushing and flossing practices often fail to reach, loosen and remove deep-gum and/or deep inter-dental food particulate, plaque or biofilm. Most individuals have professional dental cleanings biannually to remove tarter deposits.

For many years products have been devised to facilitate the simple home cleaning of teeth, although as yet a single device which is simple to use and cleans all surfaces of a tooth and/or the gingival or sub-gingival areas simultaneously is not available. The conventional toothbrush is widely utilized, although it requires a significant input of energy to be effective and, furthermore, a conventional toothbrush cannot adequately clean the inter-proximal areas of the teeth. Cleaning of the areas between teeth currently requires the use of floss, pick, or some such other additional device apart from a toothbrush.

Electric toothbrushes have achieved significant popularity and, although these reduce the energy input required to utilize a toothbrush, they are still inadequate to ensure proper inter-proximal tooth cleaning. Oral irrigators are known to clean the inter-proximal area between teeth. However, such devices have a single jet which must be directed at the precise inter-proximal area involved in order to remove debris. These water pump type cleaners are therefore typically only of significant value in connection with teeth having braces thereupon which often trap large particles of food. It will be appreciated that if both debris and plaque are to be removed from teeth, at present a combination of a number of devices must be used, which is extremely time consuming and inconvenient.

In addition, in order for such practices and devices to be effective, a high level of consumer compliance with techniques and/or instructions is required. The user-to-user variation in time, cleaning/treating formula, technique, etc., will affect the cleaning of the teeth.

The present invention ameliorates one or more of the above mentioned disadvantages with existing oral hygiene apparatus and methods, or at least provides the market with an alternative technology that is advantageous over known technology, and also may be used to ameliorate a detrimental condition or to improve cosmetic appearance of the oral cavity.

SUMMARY OF THE INVENTION

In one aspect, the present invention provides for oral care systems comprising: an appliance comprising a first and second plurality of nozzles, the appliance configured to be held in the mouth of a user with the first and second plurality of nozzles in fluid communication with one or more surfaces of the user's oral cavity; a source of gas; a source of liquid, wherein the source of liquid and source of gas may be separate sources or may be combined into one fluid source of gas and liquid; and a fluid controller for directing fluid to and removing fluid from the appliance; wherein the system is configured to produce a series of entrained fluid pulses from the source or sources of liquid and gas; direct such pulses through a first plurality of the nozzles in the appliance to the one or more surfaces of the user's oral cavity; and remove fluid from the appliance through a second plurality of nozzles to the fluid controller.

According to another aspect, the present invention provides for oral care systems comprising: an appliance comprising a first and second plurality of nozzles, the appliance configured to be held in the mouth of a user with the first and second plurality of nozzles in fluid communication with one or more surfaces of the user's oral cavity; a source of gas; a source of liquid; and a fluid controller for directing fluid to the appliance; wherein such system is configured such that gas from the source of gas is pulsed from the fluid controller to the first plurality of nozzles in the appliance and liquid from the source of liquid is pulsed into the gas pulsed from the fluid controller at a frequency ratio (liquid/gas) of from greater than zero to about 50 to form entrained fluid between the fluid controller and the nozzles.

Other aspects of the present invention are directed to methods of cleaning, or otherwise providing benefits to, one or more surfaces of the oral cavity using a system of the present invention.

DETAILED DESCRIPTION OF THE INVENTION

Figure 1:
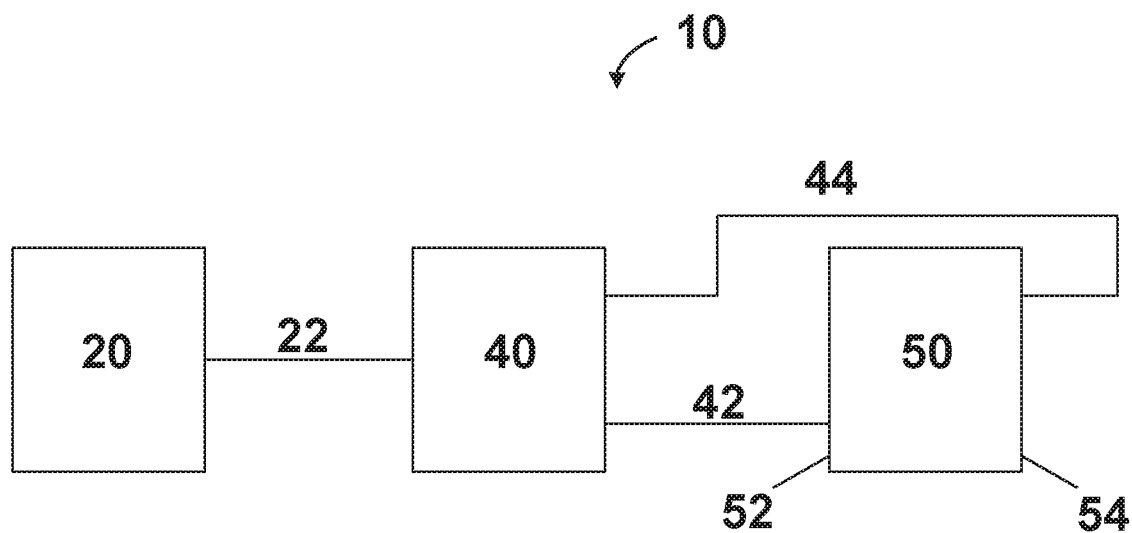
FIG. 1 is a schematic drawing of a first embodiment of a system according to the present invention.

Applicants have recognized that entrained fluid may be used in accord with the systems and methods of the present invention to achieve significant beneficial effect in the oral cavity. According to certain embodiments of the present invention, applicants have discovered that entrained fluid may be used in a system comprising: (a) an appliance with a first and second plurality of nozzles, the appliance configured to be held in the mouth with the nozzles in fluid communication with one or more surfaces of the oral cavity, and (b) a fluid controller, to achieve beneficial effect by directing the entrained fluid through the first plurality of nozzles and into the oral cavity and removing fluid from the oral cavity through the second plurality of nozzles. In certain embodiments, such system may be further used to reciprocate entrained fluid back and forth across the surfaces of the oral cavity. For example, the fluid controller may operate to alternately: (i) direct entrained fluid through the first plurality of nozzles of the appliance while simultaneously applying vacuum to the second plurality of nozzles to remove fluid from the appliance; and (ii) direct entrained fluid through the second plurality of nozzles of the appliance while simultaneously applying vacuum to the first plurality of nozzles to remove fluid from the appliance.

According certain other embodiments, applicants have demonstrated the unexpected superior benefits associated with pulsing entrained fluid onto surfaces of the oral cavity through at least one nozzle using certain system parameters, such as, for example, liquid/gas pulse frequency ratio. These embodiments and others, as well as, the benefits associated therewith are further described herein below.

Entrained Fluid

The term "entrained fluid" as used herein, refers broadly to gas-entrained liquid and liquid-entrained gas. As will be recognized by one of skill in the art, "gas-entrained liquid" refers to gas and liquid mixed such that small particles of the gas are dispersed in the liquid, while "liquid-entrained gas" refers to gas and liquid mixed such that small particles of the liquid are dispersed in the gas. In certain embodiments, the systems and methods of the present invention use liquid-entrained gas. In certain other embodiments, the systems and methods of the present invention use gas-entrained liquid.

According to certain embodiments, the present invention comprises a system configured to produce entrained fluid from a source of gas and a source of liquid, wherein the source of gas and source of liquid may be separate sources or may be combined to form a single fluid source of gas and liquid. The sources of gas and/or liquid in the present invention may each comprise a reservoir, tank, or other container suitable for holding the gas and/or liquid, or may comprise a closeable gas or liquid pipe, line, hose or other closeable continuous source of gas and/or liquid. In certain embodiments, the source of gas and source of liquid are combined to form a single fluid source of gas and liquid, including for example, a pressurized tank of the gas and liquid. In certain other embodiments, the source of gas and source of liquid are separate individual sources of gas and liquid selected from the group consisting of reservoirs, tanks, and the like.

As illustrated and described in further detail below, according to certain embodiments of the present invention, the gas or liquid may be entrained within the other to form entrained fluid that is subsequently introduced to and pulsed from a fluid controller to an appliance comprising nozzles in fluid communication with the oral cavity. For example, entrained fluid may be dispensed from a combined source of gas and liquid to a fluid controller which subsequently dispenses the entrained fluid to the appliance.

Alternately, gas and liquid provided from separate sources within the system may be combined in accord with the present invention to form entrained fluid that is then introduced to an appliance.

According to other embodiments, as further described below, the gas and liquid may be combined to form entrained fluid within the appliance. For example, gas from a gas source may be pulsed to an appliance while liquid from a liquid source is streamed or pulsed to the appliance. The entrained fluid is formed when the gas and liquid are combined in the appliance.

Any of a variety of suitable gases and liquids may be used to produce entrained fluids for use in accord with the present invention. Examples of suitable gases include, but are not limited to, air, nitrogen, argon, carbon dioxide, oxygen, nitrous oxide, nitric oxide, mixtures of two or more thereof and the like. In certain embodiments, the gas comprises air. In certain embodiments, the gas comprises nitrogen.

Any liquid suitable for producing entrained fluids for use in the oral cavity may be used in the present invention. In certain embodiments, the liquid will be, or will comprise, water. In certain embodiments, the composition comprises from about 60% to about 99.99% water, including from about 70% to about 95% water, from about 80% to 95% water, from about 60% to about 90% water, from about 60% to about 80% water, or from about 60% to about 75% water. In certain embodiments, the liquid may be a composition comprising alcohol. Any of a variety of alcohols represented by the formula $R_4$—OH, wherein $R_4$ is an alkyl group having from 2 to 6 carbons, may be used in the liquid of the present invention. Examples of suitable alcohols of formula $R_4$—OH include ethanol; n-propanol, iso-propanol; butanols; pentanols; hexanols, and combinations of two or more thereof, and the like. In certain embodiments, the alcohol is, or comprises, ethanol. In some embodiments, the alcohol may be present in the liquid composition in an amount of at least about 10.0% v/v of the total composition, or from about 10% to about 35% v/v of the total composition, or from about 15% to about 30% v/v of the total composition and may be from about 20% to about 25% v/v of the total composition. In other embodiments, the liquid composition may comprise a reduced level of alcohol. The phrase "reduced level" of alcohol means an amount of a $R_4$—OH alcohol of about 10% v/v or less, optionally of about 5% v/v or less, optionally of about 1% v/v or less, optionally of about 0.1% v/v or less by volume of the total composition. In certain embodiments, the compositions of the present invention are free of $R_4$—OH alcohols.

In certain embodiments, the liquid is a composition comprising at least one ingredient, or agent, effective for providing the beneficial effect sought, in an amount effective to provide the beneficial effect when contacted with the surfaces of the oral cavity. For example, the liquid may include, without limitation, an ingredient selected from the group consisting of antimicrobial agents, whitening agents, cleaning agents, mineralization agents, desensitizing agents, and combinations of two or more thereof.

Examples of suitable antimicrobial agents which may be employed include, without limitation, essential oils, including but not limited to menthol, thymol, eucalyptol, methyl salicylate, and combinations of two or more thereof, cetyl pyidium chloride (CPC), chlorhexidine, hexetidine, chitosan, triclosan, domiphen bromide, stannous fluoride, soluble pyrophosphates, metal oxides including but not limited to zinc oxide, peppermint oil, sage oil, sanguinaria, dicalcium dihydrate, aloe vera, polyols, protease, lipase, amylase, metal salts including but not limited to zinc citrate, and combinations of two or more thereof and the like.

Examples of suitable whitening agents include, but are not limited to, hydrogen peroxide, carbamide peroxide, other agents capable of generating hydrogen peroxide when applied to the teeth, abrasives such as silica, sodium bicarbonate, alumina, apatites, bioglass, and combinations of two or more thereof. In certain embodiments, the liquid composition comprises silica.

Any of a variety of additional surfactants may be used in a liquid composition present invention. Suitable surfactants may include anionic, non-ionic, cationic, amphoteric, zwitterionic surfactants, and combinations of two or more thereof. Examples of suitable surfactants are disclosed, for example, in U.S. Pat. No. 7,417,020 to Fevola, et al which is incorporated in its entirety herein by reference.

In certain embodiments, the compositions of the present invention comprise a non-ionic surfactant. Those of skill in the art will recognize that any of a variety of one or more non-ionic surfactants include, but are not limited to, compounds produced by the condensation of alkylene oxide groups (hydrophilic in nature) with an organic hydrophobic compound which may be aliphatic or alkyl-aromatic in nature. Examples of suitable non-ionic surfactants include, but are not limited to, alkyl polyglucosides; alkyl glucose amines, block copolymers such as ethylene oxide and propylene oxide copolymers e.g. Poloxamers; ethoxylated hydrogenated castor oils available commercially for example under the trade name CRODURET (Croda Inc., Edison, N.J.); alkyl polyethylene oxide e.g. Polysorbates, and/or; fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and mixtures thereof.

Exemplary non-ionic surfactants are selected from the group known as poly(oxyethylene)-poly(oxypropylene) block copolymers. Such copolymers are known commercially as poloxamers and are produced in a wide range of structures and molecular weights with varying contents of ethylene oxide. These non-ionic poloxamers are non-toxic and acceptable as direct food additives. They are stable and readily dispersible in aqueous systems and are compatible with a wide variety of formulations and other ingredients for oral preparations. These surfactants should have an HLB (Hydrophilic-Lipophilic Balance) of between about 10 and about 30 and preferably between about 10 and about 25. By way of example, non-ionic surfactants useful in this invention include the poloxamers identified as poloxamers 105, 108, 124, 184, 185, 188, 215, 217, 234, 235, 237, 238, 284, 288, 333, 334, 335, 338, 407, and combinations of two or more thereof. In certain preferred embodiments, the composition comprises poloxamer 407.

In certain embodiments, the compositions of the claimed invention comprise less than about 9% of non-ionic surfactant, less than 5%, or less than 1.5%, or less than 1%, or less than 0.8, less than 0.5%, less than 0.4%, or less than 0.3% of non-ionic surfactants. In certain embodiments, the composition of the present invention is free of non-ionic surfactants.

In certain embodiments, the compositions of the present invention also contain at least one alkyl sulfate surfactant. In certain embodiments, suitable alkyl sulfate surfactants include, but are not limited to sulfated $C_8$ to $C_{18}$, optionally sulfated $C_{10}$ to $C_{16}$ even numbered carbon chain length alcohols neutralized with a suitable basic salt such as sodium carbonate or sodium hydroxide and mixtures thereof such that the alkyl sulfate surfactant has an even numbered $C_8$ to $C_{18}$, optionally $C_{10}$ to $C_{16}$, chain length. In certain embodiments, the alkyl sulfate is selected from the group consisting of sodium lauryl sulfate, hexadecyl sulfate and mixtures thereof. In certain embodiments, commercially available mixtures of alkyl sulfates are used. In certain embodiments, the alkyl sulfate surfactant is present in the composition from about 0.001% to about 6.0% w/v, or optionally from about 0.1% to about 0.5% w/v of the composition.

Another suitable surfactant is one selected from the group consisting of sarcosinate surfactants, isethionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate. The sarcosinate surfactant may be present in the compositions of the present invention from about 0.1% to about 2.5%, or from about 0.5% to about 2% by weight of the total composition.

Zwitterionic synthetic surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

The amphoteric surfactants useful in the present invention include, but are not limited to, derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of suitable amphoteric surfactants include, but are not limited alkylimino-diproprionates, alky lamphoglycinates (mono or di), alkylamphoproprionates (mono or di), alkylamphoacetates (mono or di), N-alkyl [3-aminoproprionic acids, alkylpolyamino carboxylates, phosphorylated imidazolines, alkyl betaines, alkylamido betaines, alkylamidopropyl betaines, alkyl sultaines, alkylamido sultaines, and mixtures thereof. In certain embodiments, the amphoteric surfactant is selected from the group consisting of alkylamidopropyl betaines, amphoacetates such as sodium auroamphoacetate and mixtures thereof. Mixtures of any of the above mentioned surfactants can also be employed. A more detailed discussion of anionic, nonionic and amphoteric surfactants can be found in U.S. Pat. No. 7,087,650 to Lennon; U.S. Pat. No. 7,084,104 to Martin et al.; U.S. Pat. No. 5,190,747 to Sekiguchi et al.; and U.S. Pat. No. 4,051,234, Gieske, et al., each of which patents are herein incorporated by reference in their entirety.

In certain embodiments, the compositions of the claimed invention comprise less than about 9% of amphoteric surfactant, less than 5%, or less than 1.5%, or less than 1%, or less than 0.8, less than 0.5%, less than 0.4%, or less than 0.3% of amphoteric surfactants. In certain embodiments, the composition of the present invention is free of amphoteric surfactants.

Additional surfactants may be added with the alkyl sulfate surfactant to aid in solubilization of the essential oils provided such surfactants do not affect the bioavailability of the essential oils. Suitable examples include additional anionic surfactants, nonionic surfactants, amphoteric surfactants and mixtures thereof. However, in certain embodiments, the total surfactant concentration (including the alkyl sulfate surfactant alone or in combination with other surfactants) for mouth rinses of the present invention should not exceed or should about 9% or less, optionally, the total surfactant concentration should be about 5% or less, optionally about 1% or less, optionally about 0.5% or less w/w % of active surfactant by weight of the composition.

In certain embodiments, a sugar alcohol (humectant) is also added to the oral compositions of the present invention. The sugar alcohol solvent(s) may be selected from those multi-hydroxy-functional compounds that are conventionally used in oral and ingestible products. In certain embodiments, the sugar alcohol (s) should be nonmetabolized and non-fermentable sugar alcohol (s). In specific embodiments, the sugar alcohols include, but are not limited to sorbitol, glycerol, xylitol, mannitol, maltitol, inositol, allitol, altritol, dulcitol, galactitol, glucitol, hexitol, iditol, pentitol, ribitol, erythritol and mixtures thereof. Optionally, the sugar alcohol is selected from the group consisting of sorbitol and xylitol or mixtures thereof. In some embodiments, the sugar alcohol is sorbitol. In certain embodiments, the total amount of sugar alcohol (s), which are added to effectively aid in the dispersion or dissolution of the mouth rinse or other ingredients, should not exceed about 50% w/of the total composition. Or, total amount of sugar alcohol should not exceed about 30% w/v of the total composition. Or, total amount of sugar alcohol should not exceed 25% w/v of the total composition. The sugar alcohol can be in an amount of from about 1.0% to about 24% w/v, or from about 1.5% to about 22% w/v, or from about 2.5% to about 20% w/v of the total composition.

In certain embodiments, a polyol solvent is added to the composition. The polyol solvent comprises a polyol or polyhydric alcohol selected from the group consisting of polyhydric alkanes (such as propylene glycol, glycerin, butylene glycol, hexylene glycol, 1,3-propanediol); polyhydric alkane esters (dipropylene glycol, ethoxydiglycol); polyalkene glycols (such as polyethylene glycol, polypropylene glycol) and mixtures thereof. In certain embodiments, the polyol solvent can be present in an amount of from 0% to about 40% w/v, or from about 0.5% to about 20% w/v, or from about 1.0% to about 10% w/v of the composition.

Sweeteners such as aspartame, sodium saccharin (saccharin), sucralose, stevia, acesulfame K and the like may be added for better taste in amounts of from about 0.0001% w/v to about 1.0% w/v. In certain preferred embodiments, the sweetener comprises sucralose.

In certain embodiments, the composition further comprises flavors or flavorants to modify or magnify the taste of the composition, or reduce or mask the sharp "bite" or "burn" of ingredients such as thymol. Suitable flavors include, but are not limited to, flavor oils such as oil of anise, anethole, benzyl alcohol, spearmint oil, citrus oils, vanillin and the like may be incorporated. Other flavors such as citrus oils, vanillin and the like may be incorporated to provide further taste variations. In these embodiments, the amount of flavor oil added to the composition can be from about 0.001% to about 5% w/v, or from about 0.01% to about 0.3% w/v of the total composition. The particular flavors or flavorants, and other taste improving ingredients, employed will vary depending upon the particular taste and feel desired. Those skilled in the art can select and customize these types of ingredients to provide the desired results.

In certain embodiments, acceptably approved food dyes may be used to provide a pleasing color to the compositions of the invention. These may be selected from, but not limited to, the long list of acceptable food dyes. Suitable dyes for this purpose include FD&C yellow #5, FD&C yellow #10, FD&C blue #1 and FD&C green #3. These are added in conventional amounts, typically in individual amounts of from about 0.00001% w/v to about 0.0008% w/v, or from about 0.000035% w/v to about 0.0005% w/v of the composition.

Other conventional ingredients may be used in the liquid or mouth rinse compositions of this invention, including those known and used in the art. Examples of such ingredients include thickeners, suspending agents and softeners. Thickeners and suspending agents useful in the compositions of the present invention can be found in U.S. Pat. No. 5,328,682 to Pullen et al., herein incorporated by reference in its entirety. In certain embodiments, these are incorporated in amounts of from about 0.1% w/v to about 0.6% w/v, or about 0.5% w/v of the composition.

In certain embodiments of the present invention the liquid for use in the present invention is a mouthwash liquid comprising water and one or more essential oils selected from the group consisting of menthol, thymol, eucalyptol, methyl salicylate and combinations of two or more thereof. In certain embodiments, the mouthwash liquid comprising water and all four essential oils menthol, thymol, eucalyptol, and methyl salicylate. In certain embodiments, the mouthwash liquid further comprises at least one surfactant. In certain embodiments the mouthwash liquid further comprises ethanol. In certain embodiments, the mouthwash liquid is free of ethanol.

In certain embodiments, more than one liquid may be used in the system and methods of the invention. For example, a cleaning solution may be applied to the oral cavity, followed by a second solution containing, for example, a whitening agent or an antimicrobial agent. Solutions also may include a plurality of agents to accomplish more than one benefit with a single application. For example, the solution may include both a cleansing agent and an agent for ameliorating a detrimental condition, as further discussed below. In addition, a single solution may be effective to provide more than one beneficial effect to the oral cavity. For example, the solution may include a single agent that both cleans the oral cavity and acts as an antimicrobial, or that both cleans the oral cavity and whitens teeth.

Appliance

Any suitable article that is configured to be held in the mouth of a user with at least one nozzle in fluid communication with one or more surfaces of the user's oral cavity may be used as an appliance herein. In certain embodiments, when in use, the appliance functions to receive fluid from the fluid controller which is directed through at least one nozzle therein to a user's oral cavity.

In certain embodiments, the article comprises a first and second plurality of nozzles and is configured to be held in the mouth of a user with the first and second plurality of nozzles in fluid communication with one or more surfaces of the user's oral cavity. When in use, the appliance functions to receive fluid from the fluid controller through the first plurality of nozzles onto the surfaces of the oral cavity which may then be removed from the oral cavity through the second plurality of nozzles. The appliance may also be configured such that fluid may be directed from the fluid controller through the second plurality of nozzles onto the surfaces of the oral cavity and removed from the oral cavity through the first plurality of nozzles.

In certain embodiments, the appliance comprises a mouthpiece. Any suitable mouthpiece comprising at least one nozzle and configured to be held in the mouth to introduce fluid into the oral cavity in accord with this invention may be used. In certain embodiments, the mouthpiece comprises a first manifold in fluid communication with at least one nozzle such that fluid from the fluid controller can be directed into the first manifold and from the first manifold through at least one nozzle onto the surfaces of the oral cavity. In such embodiments, the mouthpiece may further comprise a first port in fluid communication with the first manifold through which fluid from the fluid controller is directed to the first manifold. Several mouthpiece embodiments will be described later in this disclosure.

In certain embodiments, the mouthpiece comprises a first and second manifold in fluid communication with a first and second plurality of nozzles, respectively, such that fluid from the fluid controller can be directed into the first manifold and from the first manifold through a first plurality of nozzles onto the surfaces of the oral cavity and/or fluid can be removed from the oral cavity through the first plurality of nozzles and through the first manifold. Likewise, fluid may be directed to the oral cavity from the fluid communicator through the second manifold and second plurality of nozzles and/or removed from the oral cavity through the second plurality of nozzles and then the second manifold. The mouthpiece may further comprise first and second ports in fluid communication with the first and second manifolds, respectively.

The mouthpiece may be comprised of multiple components. The mouthpiece comprises a chamber for maintaining the entrained fluid proximate the plurality of surfaces, i.e. fluid-contacting-chamber (FCC). By "proximate", it is meant that the fluid contacts the surfaces. The FCC is defined by the space bounded by the front inner wall and rear inner wall of the appliance, and a wall, or membrane, extending between and integral with the front and rear inner walls of the appliance, and in certain embodiments, an optional rear gum-sealing membrane. Together, the front and rear inner walls, and the wall extending there between form the FCC. The general shape of the FCC is that of a "U" or an "n", depending on the orientation of the appliance, which follows the teeth to provide uniform and optimized contact by the fluid. The FCC may be flexible or rigid depending on the particular appliance. The front and rear inner walls of the FCC each include a plurality of openings, or slots, or nozzles through which entrained fluid is directed to contact the plurality of surfaces of the oral cavity.

The FCC design may be optimized for maximum effectiveness as it relates to the size, shape, thickness, materials, volume created around the teeth/gingiva, nozzle design and placement as it relates to the oral cavity and the teeth in conjunction with the manifold and gingival margin seal to provide comfort and minimize the gagging reflex of the user. The combination of the above provides effective contact of the teeth and gingival area by the entrained fluid.

The FCC provides a controlled and isolated, or semi-isolated, environment, i.e. the FCC, to contact teeth and/or gingival area with entrained fluids, and preferably to remove spent fluids, as well as debris, plaque, etc., from the FCC. The FCC also allows increased flow rates and pressure of fluids without drowning the individual nozzles when significant flow rates are required to provide adequate cleaning, for example. The FCC also allows reduced fluid quantities and flow rates when required, as only the area within the FCC is being contacted with entrained fluid, not the entire oral cavity. The FCC also allows controlled delivery and duration of contact of entrained fluid on, through and around teeth and the gingival area, allowing increased concentrations of fluids on the area being contacted by the fluid, thereby providing more effective control and delivery of entrained fluid.

The device may incorporate a switching mechanism, which would allow it to be operable only when in the correct position in the mouth. In some embodiments, the appliance may include both upper and lower sections to provide substantially simultaneous contact of the plurality of surfaces of the oral cavity by entrained fluid.

The number and location of openings, also referred to herein as nozzles, contained within the inner walls of the appliance through which the entrained fluid is directed will vary and be determined based upon the circumstances and environment of use, the particular user and the beneficial effect being sought. The cross-sectional geometry of the openings may be circular, elliptical, trapezoidal, or any other geometry that provides effective contact of the surfaces of the oral cavity by the fluid. The location and number of openings may be designed to direct jets of entrained fluid in a variety of spray patterns effective for providing the desired beneficial effect. In certain embodiments, opening diameters may be from about 0.1 to about 3 mm, or from about 0.35 mm to about 0.8 mm, or about 0.5 mm, to provide effective cleaning and average jet velocities and coverage. The number of nozzles for simultaneous jet can be from 1 to 500, or 100-300. The horizontal spacing, or distance between the nozzles can be 0.5 mm to 25 mm, or 1 mm to 10 mm, or 3 mm. Average jet velocities are about 0.5 m/s to about 100 m/s, or about 1 m/s to about 50 m/s. Nozzle coverage ranges from about 1 $mm^2$ to about 20 $mm^2$, or about 1 $mm^2$ to about 10 $mm^2$, or about 1 $mm^2$ to about 5 $mm^2$. The volume of each pulse from each nozzle is about 0.1 microliter to about 5 ml, or about 0.1 microliter to about 1 ml, or about 5 microliter to about 100 microliter.

Optimal opening placement and direction/angles allows coverage of substantially all teeth surfaces in the area if the oral cavity to be contacted by entrained fluid, including but not limited to interdental, top, side, back, and gingival pocket surfaces. In alternate embodiments, the openings could be of different sizes and different shapes to provide different cleaning, coverage and spray patterns, to adjust velocities, density and fan patterns (full cone, fan, partial, cone, jet), or due to formulation consideration. Nozzles could also be designed to be tubular and or extend from the FCC membrane to provide directed spray, or act as sprinkler like mechanism to provide extended coverage across the teeth, similar to a hose sprinkler system. The nozzles are preferably integral to the inner walls of the FCC membrane and can be incorporated into the inner walls through any number of assembly or forming techniques known in the art (insert molded, formed in membrane through machining, injection molding, etc.).

The FCC may be an elastomeric material such as ethylene vinyl acetate (EVA), thermoplastic elastomer (TPE), or silicone, to allow motion of the inner walls and provide a greater jet coverage area with minimal mechanics, reducing the volumetric flow requirements to achieve optimized performance, while providing a softer and more flexible material to protect the teeth if direct contact with the teeth is made. A flexible membrane may also provide acceptable fitment over a large range of users, due to its ability to conform to the teeth. Alternatively, the FCC could be made of a rigid or semi-rigid material, such as but not limited to a thermoplastic.

In an alternate embodiment, the FCC could also include abrasive elements such as filaments, textures, polishing elements, additives (silica, etc.), and other geometric elements that could be used for other cleaning and/or treatment requirements as well as ensuring minimal distance between the teeth and FCC for, but not limited to, treatment, cleaning, and positioning.

The FCC could be created via a variety of methods such as, but not limited to, machining, injection molding, blow molding, extrusion, compression molding, and/or vacuum forming. It can also be created in conjunction with the manifold, but incorporating the manifold circuitry within the FCC, and/or over-molded onto the manifold to provide a unitary construction with minimal assembly.

In one embodiment, the FCC may be fabricated separately and then assembled to the manifolds, utilizing any number of assembling and sealing techniques, including adhesives, epoxies, silicones, heat sealing, ultrasonic welding, and hot glue. The FCC is designed in a way that, when assembled with the manifold, it effectively and efficiently creates the preferred dual manifold design without any additional components.

In certain embodiments, the FCC can also be designed or used to create the gingival sealing area. In certain embodiments, a vacuum is applied within the FCC, which improves the engagement of the mouthpiece to form a positive seal with the gingival in the oral cavity. In other embodiments, a pressure is applied outside the FCC, within the oral cavity, which improves the engagement of the appliance to form a positive seal with the gingival in the oral cavity. In yet other embodiments, a denture-like adhesive may be applied around the mouthpiece during the initial use to provide a custom reusable resilient seal when inserted into the oral cavity for a particular user. It would then become resiliently rigid to both conform and provide a positive seal with the guns and on subsequent applications. In another embodiment, the seal could be applied and/or replaced or disposed of after each use.

The mouthpiece also comprises a first manifold for containing the entrained fluid and for providing the fluid to the FCC through the openings of the front inner wall, and a second manifold for containing the entrained fluid and for providing the fluid to the chamber through the openings of the rear inner wall. This design provides a number of different options, depending on what operation is being conducted. For instance, in a cleaning operation, it may be preferable to deliver jets of entrained fluid into the FCC directly onto the teeth from one side of the FCC from the first manifold and then evacuate/pull the fluid around the teeth from the other side of the FCC into the second manifold to provide controlled interdental, gum line and surface cleaning. This flow from the one side of the FCC could be repeated a number of times in a pulsing action before reversing the flow to deliver jets of entrained fluid from the second manifold and evacuating/pulling the fluid through the back side of the teeth into the first manifold for a period of time and/or number of cycles. Such fluid action creates a turbulent, repeatable and reversible flow, thus providing reciprocation of the fluid about the surfaces of the oral cavity. For example, the fluid controller may operate to alternately: (i) direct entrained fluid through the first plurality of nozzles of the appliance while simultaneously applying vacuum to the second plurality of nozzles to remove fluid from the appliance; and (ii) direct entrained fluid through the second plurality of nozzles of the appliance while simultaneously applying vacuum to the first plurality of nozzles to remove fluid from the appliance. The terms "reciprocating movement of fluid(s)" and "reciprocation of fluid(s)" are used interchangeably herein. As used herein, both terms mean alternating the direction of flow of the entrained fluid(s) back and forth over surfaces of the oral cavity of a mammal from a first flow direction to a second flow direction that is opposite the first flow direction.

In alternate embodiments, the manifold can be of single manifold design providing pushing and pulling of the entrained fluid through the same sets of jets simultaneously, or can be any number of manifold divisions to provide even greater control of the fluid delivery and removal of the cleaning and fluid treatment. In the multi-manifold also can be designed to have dedicated delivery and removal manifolds. The manifolds can also be designed to be integral to and/or within the FCC.

The material for the manifold would be a semi-rigid thermoplastic, which would provide the rigidity necessary not to collapse or burst during the controlled flow of the fluids, but to provide some flexibility when fitting within the user's mouth. To minimize fabrication complexity, number of components and tooling cost, the dual manifold is created when assembled with the FCC. The manifold could also be multi-component to provide a softer external "feel" to the teeth/gums utilizing a lower durometer elastomeric material, such as, but not limited to, a compatible thermoplastic elastomer (TPE). The manifold could be created via a variety of methods such as, but not limited to machining, injection molding, blow molding, compression molding, or vacuum forming.

As shown, the appliance also comprises a first port for conveying the fluid to and from the first manifold and a second port for conveying the fluid to and from the second manifold, and means for providing an effective seal of the directing means within the oral cavity, i.e. a gingival seal. In certain embodiments, the first and second ports may serve both to convey fluid to and from the first and second manifolds and to attach the appliance to the means for providing fluid to the appliance.

As noted above and described in more detail below, in certain embodiments, the system of the present invention is configured such that two sources of liquid and/or gas are combined to form entrained fluid between the fluid controller and the nozzles, e.g. before or within one or more of the manifolds and/or ports of the appliance. In certain of such embodiments, the appliance comprises a manifold and/or port configured (a) to receive a gas pulsed from the fluid controller directed to at least one nozzle and (b) to allow a separate liquid to be combined with the pulse within the manifold and/or port to form an entrained fluid directed to at least one nozzle.

Fluid Controller

Any fluid controller suitable for directing fluid to at least one nozzle of an appliance in accord with the present invention may be used herein. In general, the fluid controller will comprise one or more portals, passages, and/or conduits, or the like, through which fluid may be received and conveyed to achieve the desired functions of the claimed invention, e.g. receiving fluid from a fluid source; and/or directing fluid to at least one nozzle of an appliance; and/or removing fluid from an appliance. In certain embodiments, the fluid controller may comprise, or otherwise be controlled by, a logic circuit and/or mechanically controlled circuit. In certain embodiments, the fluid controller may comprise, or otherwise be powered by, a power source, such as but not limited to, electricity provided through a plug, batteries, whether rechargeable or disposable, and the like.

In certain embodiments, the fluid controller comprises a reciprocating flow controller. In general the reciprocating flow controller is designed to alternate the flow of fluid to different portions of the appliance to allow for reciprocating flow of fluid across one or more surfaces of the oral cavity therein. For example, in certain embodiments, the reciprocating flow controller may have a first position which directs fluid to a first manifold and through at least a first nozzle of an appliance into the oral cavity in a first direction, and a second position which directs fluid to a second manifold and through at least a second nozzle of an appliance into the oral cavity in a second direction. The reciprocating flow controller may alternate between these two positions to alternate the flow of fluid in the appliance and thereby reciprocate fluid across the surfaces of the oral cavity within the appliance. Several reciprocating flow controller embodiments will be described later in this disclosure.

Device/System

In certain embodiments, devices of the present invention may include a means for attaching or connecting the device to a reservoir for containing the liquid, gas, or the liquid/gas blend. The reservoir may be removably attached to the device. In this case, the reservoir and the device may comprise means for attaching one to the other. After completion of the process, the reservoir may be discarded and replaced with a different reservoir, or may be refilled and used again. In other embodiments, the device will include a reservoir integral with the device. In embodiments where the device may be attached to a base unit, as described herein, the reservoir, whether integral with the device or removably attached to the device, may be refilled from a supply reservoir which forms a part of the base unit. Where a base unit is utilized, the device and the base unit will comprise means for attaching one to the other.

The device will comprise a power source for powering one or more components of the device. The power source may be contained within the device, e.g. in the handle of the device, for example, batteries, whether rechargeable or disposable. Where a base unit is employed, the base may include the power source. In other embodiments, the base unit may include a charger for recharging batteries contained within the device. In another embodiment, compressed gas, such as in the form of a pressurized cartridge could be used as the power source for powering one or more components of the device. The cartridge could be disposable after one or more uses, or could be repressurized for subsequent uses.

In certain embodiments, the devices of the present invention include the appliance as a non-removable part of the device. In other embodiments, the appliance is removeably attached to the device via one or more connectors. In such embodiments, multiple users may attachez and use their own separate appliances with the device.

As used herein, "means for conveying fluid" includes structures through which liquid, gas, or entrained fluid may travel or be transported throughout the systems according to the invention and includes, without limitation passages, conduits, tubes, ports, portals, channels, lumens, pipes and manifolds. Such means for conveying fluids may be utilized in devices for providing reciprocation of entrained fluids and means for directing entrained fluids onto and about surfaces of the oral cavity. Such conveying means also provide fluid to the directing means and provides gas, liquid, and/or entrained fluid to the reciprocation means from a reservoir for containing gas, liquid, or entrained fluid, whether the reservoir is contained within a hand-held device containing the reciprocation means or a base unit. The conveying means also provides liquid or gas from a base unit to reservoirs contained within the hand-held device. Described herein are methods, devices and systems useful in providing a beneficial effect to an oral cavity of a mammal, e.g. a human.

Methods entail contacting a plurality of surfaces of the oral cavity with a entrained fluid that is effective for providing the desired beneficial effect to the oral cavity. In such methods, reciprocation of the entrained fluid(s) over the plurality of surfaces of the oral cavity is provided under conditions effective to provide the desired beneficial effect to the oral cavity. Contact of the plurality of surfaces by the entrained fluid may be conducted substantially simultaneous. By substantially simultaneous, it is meant that, while not all of the plurality of surfaces of the oral cavity are necessarily contacted by the entrained fluid at the same time, the majority of the surfaces are contacted simultaneously, or within a short period of time to provide an overall effect similar to that as if all surfaces are contacted at the same time.

The conditions for providing the desired beneficial effect in the oral cavity may vary depending on the particular environment, circumstances and effect being sought. The different variables are interdependent in that they create a specific velocity of the entrained fluid. The velocity requirement may be a function of the formulation in some embodiments. For example, with change in the viscosity, additives, e.g. abrasives, shear thinning agents, etc., and general flow properties of the formulation, velocity requirements of the jets may change to produce the same level of efficacy. Factors which may be considered in order to provide the appropriate conditions for achieving the particular beneficial effect sought include, without limitation, the velocity and/or flow rate and/or pressure of the entrained fluid stream, pulsation of the entrained fluid, the spray geometry or spray pattern of the entrained fluid, the temperature of the entrained fluid and the frequency of the reciprocating cycle of the fluid. In some embodiments, the fluid flow rate (total all nozzles/simultaneous pulse) may be from about 0.1 microliter to about 15 ml, or about 0.1 microliter to about 5 ml.

Once having the benefit of this disclosure, one skilled in the art will recognize that the various factors may be controlled and selected, depending on the particular circumstances and desired benefit sought.

In addition to generally improving the oral hygiene of the oral cavity by cleaning, for example, removal or disruption of plaque build-up, food particles, biofilm, etc., the inventions are useful to ameliorate detrimental conditions within the oral cavity and to improve the cosmetic appearance of the oral cavity, for example whitening of the teeth. Detrimental conditions may include, without limitation, caries, gingivitis, inflammation, symptoms associated with periodontal disease, halitosis, sensitivity of the teeth and fungal infection. The liquids themselves may be in various forms, provided that they have the flow characteristics suitable for use in devices and methods of the present invention. For example, the liquids may be selected from the group consisting of solutions, emulsions and dispersions. In certain embodiments, the liquid may comprise a particulate, e.g. an abrasive, dispersed in a liquid phase, e.g. an aqueous phase. In such cases, the abrasive would be substantially homogeneously dispersed in the aqueous phase in order to be applied to the surfaces of the oral cavity. In other embodiments, an oil-in-water or water-in-oil emulsion may be used. In such cases, the liquid will comprise a discontinuous oil phase substantially homogeneously dispersed within a continuous aqueous phase, or a discontinuous aqueous phase substantially homogenously dispersed in a continuous oil phase, as the case may be. In still other embodiments, the liquid may be a solution whereby the agent is dissolved in a carrier, or where the carrier itself may be considered as the agent for providing the desired beneficial effect, e.g., an alcohol or alcohol/water mixture, usually having other agents dissolved therein.

Disclosed herein are systems, e.g. systems comprising oral care devices, for example a dental cleaning apparatus, suitable for in-home use and adapted to direct entrained fluid pulses onto a plurality of surfaces of a tooth and/or the gingival area, as well as methods utilizing such systems. In certain embodiments the surfaces of the oral cavity are contacted by the fluid substantially simultaneously. As used herein, reference to the gingival area includes, without limitation, reference to the sub-gingival pocket. The appropriate entrained fluid is directed onto a plurality of surfaces of teeth and/or gingival area substantially simultaneously in a reciprocating action under conditions effective to provide cleaning, and/or general improvement of the cosmetic appearance of the oral cavity and/or amelioration of a detrimental condition of the teeth and/or gingival area, thereby providing generally improved oral hygiene of teeth and/or gingival area. For example, one such device cleans teeth and/or the gingival area and removes plaque using an appropriate cleaning entrained fluid by reciprocating the entrained fluid back and forth over the front and back surfaces and inter-proximal areas of the teeth, thereby creating a cleaning cycle while minimizing the amount of cleaning fluid used.

Systems of the invention comprise devices that provide reciprocation of the entrained fluid pulses, which devices comprise a means for controlling reciprocation of the fluid. The controlling means includes means for conveying the entrained fluid to and from a means for directing the entrained fluid onto the plurality of surfaces of the oral cavity. In certain embodiments, the means for providing reciprocation of the entrained fluid comprises a plurality of portals for receiving and/or discharging the fluid, a plurality of passages, or conduits, through which the fluid is conveyed, and means for changing the direction of flow of the fluid to provide reciprocation of the fluid. The controlling means may be controlled by a logic circuit and/or a mechanically controlled circuit.

In certain embodiments, devices for providing reciprocation may include a means for attaching or connecting the device to a reservoir for containing the liquid, gas, or the liquid/gas blend. The reservoir may be removably attached to the device. In this case, the reservoir and the device may comprise means for attaching one to the other. After completion of the process, the reservoir may be discarded and replaced with a different reservoir, or may be refilled and used again. In other embodiments, the reciprocating device will include a reservoir integral with the device. In embodiments where the device may be attached to a base unit, as described herein, the reservoir, whether integral with the device or removably attached to the device, may be refilled from a supply reservoir which forms a part of the base unit. Where a base unit is utilized, the device and the base unit will comprise means for attaching one to the other.

The device will comprise a power source for driving the means for reciprocating entrained fluids. The power source may be contained within the device, e.g. in the handle of the device, for example, batteries, whether rechargeable or disposable. Where a base unit is employed, the base may include means for providing power to the device. In other embodiments, the base unit may include means for recharging the rechargeable batteries contained within the device. In another embodiment, compressed gas, such as in the form of a pressurized cartridge could be used as the power source for powering one or more components of the device. The cartridge could be disposable after one or more uses, or could be repressurized for subsequent uses.

Devices for providing reciprocation of entrained fluids will include means for attaching the device to means for directing the entrained fluid onto the plurality of surfaces of the oral cavity, e.g. an appliance such as an applicator, tray or mouthpiece. In certain embodiments, the directing means provides substantially simultaneous contact of the plurality of surfaces of the oral cavity by the fluid. The attachment means may provide removable attachment of the applicator to the device. In such embodiments, multiple users may use their own appliances with the single device comprising the reciprocating means. In other embodiments, the attachment means may provide a non-removable attachment to the appliance, whereby the appliance is an integral part of the device. Devices for providing reciprocation as described above may be contained within a housing also containing other device components so as to provide a hand-held device suitable for providing entrained fluids to the directing means, as described herein below.

FIG. 1 is a schematic drawing of a first embodiment of a system according to the present invention. The figure shows system 10, with components including: fluid supply reservoir 20, reciprocating flow controller 40, means for directing the fluid onto the plurality of surfaces of the oral cavity (appliance 50), and tubes 22, 42, and 44 for conveying the fluid throughout the system.

Tube 22 conveys fluid from reservoir 20 to reciprocating flow controller 40. Tubes 42 and 44 convey fluid from reciprocating flow controller 40 to appliance 50. Tube 42 conveys fluid to the first side 52 of appliance 50, while tube 44 conveys fluid to the second side 54 of appliance 50.

In this embodiment, fluid supply reservoir 20 contains entrained fluid. The fluid may be under sufficient pressure to be delivered to reciprocating flow controller 40, and further to appliance 50. In other embodiments, a pump, such a piston pump or rotary pump, may be located between fluid supply reservoir 20 and reciprocating flow controller 40 to supply sufficient pressure to delivered fluid to reciprocating flow controller 40, and further to appliance 50.

Fluid supply reservoir 20 may be made of glass, plastic or metal. Fluid supply reservoir 20 may be integral to system 10 and refillable. In some embodiments, fluid supply reservoir 20 may be a replaceable fluid supply, such as a single or multi-use cartridge, detachably connected to system 10.

In some embodiments, fluid supply reservoir 20 and/or tubes 22, 42, and 44 may include a heat source to pre-warm the fluid prior to direction into appliance 50 for application to the surfaces of the oral cavity. The temperature should be maintained within a range effective to provide efficacy and comfort to the user during use.

Appliance 50, discussed in detail herein below, could be integral with, or detachably connected to, reciprocating flow controller 40 by way of tubes 42, 44 and further attachment means (not shown). It could be have internally, easily cleanable filters for trapping food particles. When positioned within the oral cavity, e.g. about the teeth and gums, appliance 50 may form an effective fit or seal against the gums, and includes means to direct fluid against surfaces of the oral cavity, e.g. surfaces of the teeth.

Entrained fluid in fluid supply reservoir 20 flows through tube 22 to reciprocating flow controller 40. There may be a one-way flow valve in tube 22 to prevent back-pressure from allowing fluid flow from controller 40 back to reservoir 20. Entrained fluid flows from reciprocating flow controller 40 to appliance 50 either through tube 42 or 44, depending on the flow direction setting of flow controller 40.

In the cleaning operation, system 10 produce a series of entrained fluid pulses in appliance 50. In some embodiments flow controller 40 creates the series of entrained fluid pulses. In other embodiments, entrained fluid pulses are generated by a controller located in any of tubes 22, 42, or 44.

The actions of system 10 may be controlled by a logic circuit, which may include a program to start the reciprocation cycle, a program to execute the reciprocation cycle, i.e. to cause fluid to be reciprocated about the teeth, thereby providing the beneficial effect to the oral cavity, e.g. cleaning the teeth, a program to empty appliance 50 at the end of the reciprocation cycle, and a self-cleaning cycle to clean the system between uses, or at pre-set or automatic cleaning times.

Though not shown, a face panel with a series of switches and indicator lights may also be incorporated into system 10. Switches may include, but are not limited to, on/off, run the reciprocation program, empty system 10, and clean system 10. Indicator, or display, lights include, but are not limited to, power on, charging, reciprocation program running, system emptying, cleaning results or feedback, and self-cleaning cycle in operation. In embodiments where fluid is pre-warmed prior to direction into appliance 50, a display light could be used to indicate that the fluid is at the proper temperature for use.

One method of using system 10 to clean teeth is as follows. In the first step, the user positions appliance 50 in the oral cavity about the teeth and gingival area. In use of the system according to the invention, the user pushes a start button initiating the cleaning process. The cleaning process is as follows:

1. System 10 is activated to begin dispensing entrained fluid pulses from reservoir 20 to appliance 50 via tube 22, reciprocating flow controller 40, and tube 42. Entrained fluid is used to clean the teeth and gingival area from first side 52 of appliance 50.
2. Reciprocating flow controller 40 is then activated to change the fluid flow from tube 42 to tube 44. The pulses of entrained fluid is used to clean the teeth and gingival area from second side 54 of appliance 50.
3. To reciprocate the cleaning fluid, steps 1 and 2 are repeated as the entrained fluid pulses are used to clean the teeth and gingival area from first side 52, and then second side 54 of appliance 50, respectively.
4. The reciprocation cycle as described continues until the time required for cleaning has expired, or the desired numbers of cycles are complete.

It is noted that there may be a delay between steps 1 and 2 (in either or both, directions), allowing a dwell time where the fluid is allowed to contact the teeth without flow.

In this embodiment, entrained fluid, once it contacts the teeth and gingival surface, disperse into the oral cavity. In other embodiment, the liquid portion of the entrained fluid may be directed via tubes back to the reservoir 20 to be reused in the current, or a future cleaning process, or directed to disposal.

Figure 2:
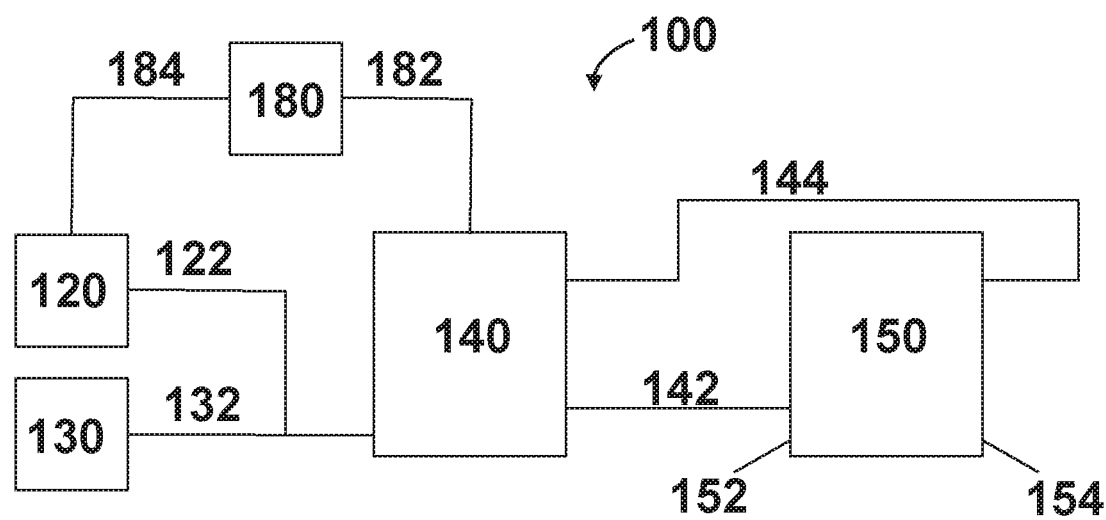
FIG. 2 is a schematic drawing of a second embodiment of a system according to the present invention.

FIG. 2 is a schematic drawing of a second embodiment of a system according to the present invention. The figure shows system 100, with components including: liquid supply reservoir 120, gas supply reservoir 130, reciprocating flow controller 140, appliance 150, vacuum pump 180, and tubes 122, 132, 142, 144, 182, and 184, for conveying the fluid throughout the system.

Tube 132 conveys gas from gas reservoir 130 to reciprocating flow controller 140. Tube 122 conveys liquid from liquid reservoir 120 to tube 132. Tubes 142 and 144 convey entrained fluid from reciprocating flow controller 140 to appliance 150. Tube 142 conveys fluid to the first side 152 of appliance 150, while tube 144 conveys fluid to the second side 152 of appliance 150.

In this embodiment, entrained fluid is created at the intersection of tubes 122 and 132, prior to reciprocating flow controller 140. Gas reservoir 130 may be under sufficient pressure to be delivered entrained fluid to reciprocating flow controller 140, and further to appliance 150. In some embodiments, liquid reservoir 120 may be under sufficient pressure, such as head pressure, to deliver liquid to the point of intersection of tubes 122 and 132. In other embodiments, a pump may be located between liquid reservoir 120 and the intersection of tubes 122 and 132 to delivered liquid to the point of intersection of tubes 122 and 132.

In some embodiments, the Venturi effect is used to entrain the liquid in the gas stream. The Venturi effect is the creation of a partial vacuum when the flow of a fluid is restricted, increasing its speed of flow. In this embodiment, gas tube 132 is narrowed at one point before widening again. Liquid tube 122 is attached to the narrowed portion of gas tube 132, and liquid in liquid tube 122 is drawn into and entrained in gas in gas tube 132.

In this embodiment, entrained fluid, once it contacts the teeth and gingival surface, separates into a gas phase and a liquid phase. The gas phase mainly disperses into the oral cavity, while the liquid phase is partially, or fully, recaptured. Tube 182 connects vacuum pump 180 to reciprocating flow controller 140. Pump 180 creates a negative pressure that draws the liquid from appliance 150 back through reciprocating flow controller 140 and delivers it back to liquid reservoir 120 via tube 184.

Liquid in liquid supply reservoir 120 flows through tube 122 to the point of intersection of tubes 122 and 132 and on to reciprocating flow controller 140. There may be a one-way flow valve in tube 122 and/or tube 132 to prevent back-pressure from allowing liquid flow back to reservoir 120, or gas to flow back to reservoir 130, respectively. After entrainment, entrained fluid flows to reciprocating flow controller 140, and then from reciprocating flow controller 140 to appliance 150 either through tube 142 or 144, depending on the flow direction setting of flow controller 140.

In the cleaning operation, system 100 produce a series of entrained fluid pulses in appliance 150. In some embodiments flow controller 140 creates the series of entrained fluid pulses. In other embodiments, entrained fluid pulses are generated by a controller located in any of tubes 122, 132, 142, or 144.

One method of using system 100 to clean teeth is as follows. In the first step, the user positions appliance 150 in the oral cavity about the teeth and gingival area. In use of the system according to the invention, the user pushes a start button initiating the cleaning process. The cleaning process is as follows:

1. System 100 is activated to begin dispensing liquid from liquid reservoir 120 and gas from gas reservoir 130 to the point of intersection of tubes 122 and 132, and on to reciprocating flow controller 140 and then appliance 150 via tube 142, reciprocating. Entrained fluid pulses are used to clean the teeth and gingival area from first side 152 of appliance 150. The entrained fluid separates into gas and liquid phases.
2. The liquid returns to reciprocating flow controller 140 via tube 144, flows to pump 180 via tube 182, and is returned to liquid reservoir 120 via tube 184.
3. Reciprocating flow controller 140 is then activated to change the fluid flow from tube 142 to tube 144. Entrained fluid pulses are used to clean the teeth and gingival area from second side 154 of appliance 150.
4. The liquid returns to reciprocating flow controller 140 via tube 142, flows to pump 180 via tube 182, and is returned to liquid reservoir 120 via tube 184.
5. To reciprocate the cleaning fluid, steps 1 through 4 are repeated as the entrained fluid pulses are used to clean the teeth and gingival area from first side 152, and then second side 154 of appliance 150, respectively.
6. The reciprocation cycle as described continues until the time required for cleaning has expired, or the desired numbers of cycles are complete.

In this embodiment, the liquid portion of the entrained fluid is directed via tube 182 back to the liquid reservoir 120 to be reused in the current, or a future cleaning process. In other embodiments, pump 180 may direct the spent liquid to disposal.

In some embodiments, entrained fluid may be delivered from reciprocating flow controller 140 to first side 152 of appliance 150 while simultaneously being drawn by vacuum pump 180 from second side 154 of appliance 150. When reciprocating flow controller 140 is activated to change the fluid flow from tube 142 to tube 144, entrained fluid may be delivered from reciprocating flow controller 140 to second side 154 of appliance 150 while simultaneously being drawn by vacuum pump 180 from first side 152 of appliance 150.

It is important to note that although 180 is termed "vacuum pump", 180 could also be used for other devices or methods for creating a pressure drop from reciprocating flow controller 140 to liquid reservoir 120. Included are devices that produce the Venturi effect or temperature drops.

Figure 3:
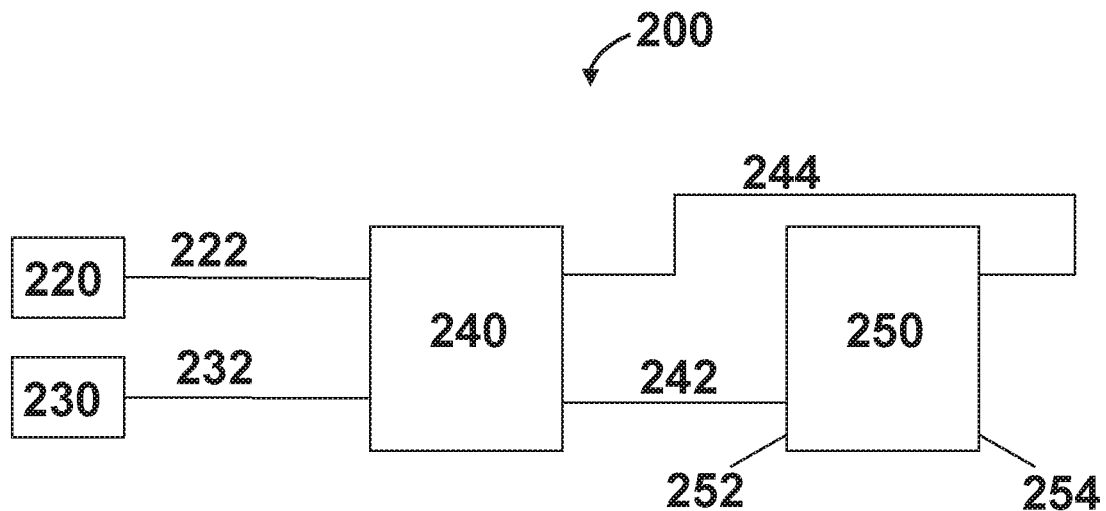
FIG. 3 is a schematic drawing of a third embodiment of a system according to the present invention.

FIG. 3 is a schematic drawing of a third embodiment of a system according to the present invention. The figure shows system 200, with components including: liquid supply reservoir 220, gas supply reservoir 230, reciprocating flow controller 240, appliance 250, and tubes 222, 232, 242, and 244, for conveying the fluid throughout the system.

Tube 222 conveys liquid from liquid reservoir 220 to reciprocating flow controller 240. Tube 232 conveys gas from gas reservoir 230 to reciprocating flow controller 240. Tubes 242 and 244 convey entrained fluid from reciprocating flow controller 240 to appliance 250. Tube 242 conveys fluid to the first side 252 of appliance 250, while tube 244 conveys fluid to the second side 25 of appliance 250.

In this embodiment, entrained fluid is created in reciprocating flow controller 240. Gas reservoir 230 may be under sufficient pressure to be delivered entrained fluid to reciprocating flow controller 240, and further to appliance 250. In some embodiments, liquid reservoir 220 may be under sufficient pressure, such as head pressure, to deliver liquid to reciprocating flow controller 240. In other embodiments, a pump may be located between liquid reservoir 220 and reciprocating flow controller 240.

In this embodiment, entrained fluid, once it contacts the teeth and gingival surface, disperse into the oral cavity. In other embodiment, some of the liquid portion of the entrained fluid may be directed via tubes back to the reservoir 220 to be reused in the current, or a future cleaning process, or directed to disposal.

Liquid in liquid supply reservoir 220 flows through tube 222 to reciprocating flow controller 240. Gas in gas reservoir 230 flows through tube 232 to reciprocating flow controller 240. There may be a one-way flow valve in tube 222 and/or tube 232 to prevent back-pressure from allowing liquid flow back to reservoir 220, or gas to flow back to reservoir 230, respectively.

After entrainment, entrained fluid flows to appliance 250 either through tube 242 or 244, depending on the flow direction setting of flow controller 240.

In the cleaning operation, system 200 produce a series of entrained fluid pulses in appliance 250. In some embodiments flow controller 240 creates the series of entrained fluid pulses. In other embodiments, entrained fluid pulses are generated by a controller located in any of tubes 222, 232, 242, or 244.

One method of using system 200 to clean teeth is as follows. In the first step, the user positions appliance 250 in the oral cavity about the teeth and gingival area. In use of the system according to the invention, the user pushes a start button initiating the cleaning process. The cleaning process is as follows:

1. System 200 is activated to begin dispensing liquid from liquid reservoir 220 to reciprocating flow controller 240 via tube 222, and gas from gas reservoir 230 to reciprocating flow controller 240 via tube 232. Reciprocating flow controller 240 sends entrained fluid to first side 252 of appliance 250 via tube 242. Entrained fluid pulses are used to clean the teeth and gingival area from first side 252 of appliance 250. The entrained fluid separates into gas and liquid phases.
2. Reciprocating flow controller 240 is then activated to change the fluid flow from tube 242 to tube 244. Entrained fluid pulses are used to clean the teeth and gingival area from second side 254 of appliance 250. The entrained fluid separates into gas and liquid phases.
3. To reciprocate the cleaning fluid, steps 1 and 2 are repeated as the entrained fluid pulses are used to clean the teeth and gingival area from first side 252, and then second side 254 of appliance 250, respectively.
4. The reciprocation cycle as described continues until the time required for cleaning has expired, or the desired numbers of cycles are complete.

In this embodiment, entrained fluid, once it contacts the teeth and gingival surface, disperse into the oral cavity. In other embodiment, the liquid portion of the entrained fluid may be directed via tubes back to the reservoir 220 to be reused in the current, or a future cleaning process, or directed to disposal.

Figure 4:
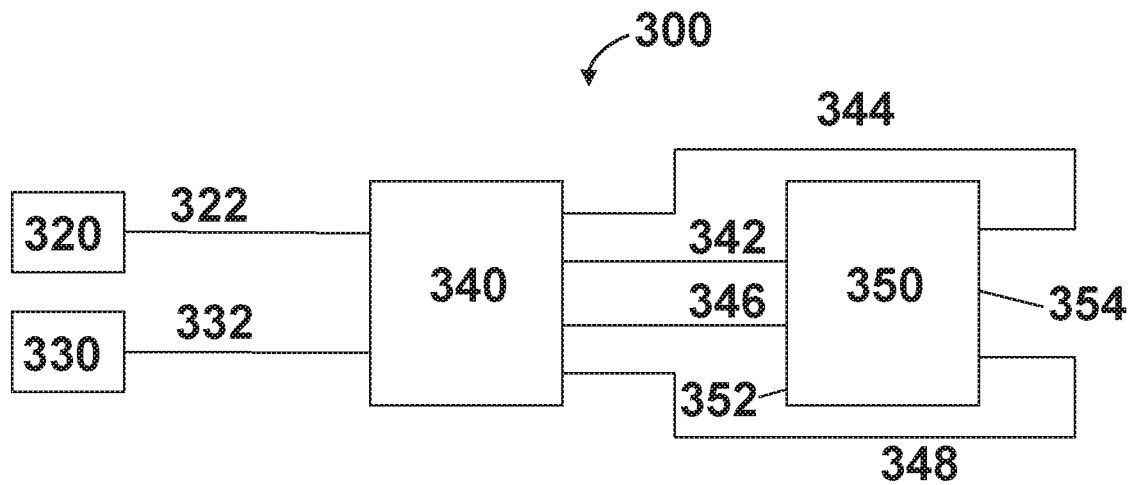
FIG. 4 is a schematic drawing of a fourth embodiment of a system according to the present invention.

FIG. 4 is a schematic drawing of a fourth embodiment of a system according to the present invention. The figure shows system 300, with components including: liquid supply reservoir 320, gas supply reservoir 330, reciprocating flow controller 340, appliance 350, and tubes 322, 332, 342, 344, 346, and 348 for conveying the fluid throughout the system.

Tube 322 conveys liquid from liquid reservoir 320 to reciprocating flow controller 340. Tube 332 conveys gas from gas reservoir 330 to reciprocating flow controller 340. Tubes 342 and 344 convey liquid from reciprocating flow controller 340 to appliance 350. Tube 342 conveys fluid to the first side 352 of appliance 350, while tube 344 conveys fluid to the second side 35 of appliance 350. Tubes 346 and 348 convey gas from reciprocating flow controller 340 to appliance 350. Tube 346 conveys gas to the first side 352 of appliance 350, while tube 348 conveys gas to the second side 354 of appliance 350.

In this embodiment, entrained fluid is created in appliance 350. Gas reservoir 330 may be under sufficient pressure to be delivered entrained fluid to appliance 350. In some embodiments, liquid reservoir 320 may be under sufficient pressure, such as head pressure, to deliver liquid to appliance 350. In other embodiments, a pump may be located between liquid reservoir 320 and reciprocating flow controller 340 to delivered liquid to appliance 350.

In this embodiment, entrained fluid, once it contacts the teeth and gingival surface, disperse into the oral cavity. In other embodiment, some of the liquid portion of the entrained fluid may be directed via tubes back to the reservoir 320 to be reused in the current, or a future cleaning process, or directed to disposal.

Liquid in liquid supply reservoir 320 flows through tube 322 to reciprocating flow controller 340. Gas in gas reservoir 330 flows through tube 332 to reciprocating flow controller 340. There may be a one-way flow valve in tube 322 and/or in tube 332 to prevent back-pressure from allowing liquid flow back to reservoir 320, or gas to flow back to reservoir 330, respectively.

In the cleaning operation, system 300 produce a series of entrained fluid pulses in appliance 350. In some embodiments flow controller 340 creates the series of entrained fluid pulses. In other embodiments, entrained fluid pulses are generated by a controller located in any of tubes 322, 332, 342, 344, 346, and 348.

One method of using system 300 to clean teeth is as follows. In the first step, the user positions appliance 350 in the oral cavity about the teeth and gingival area. In use of the system according to the invention, the user pushes a start button initiating the cleaning process. The cleaning process is as follows:

1. System 300 is activated to begin dispensing liquid from liquid reservoir 320 to reciprocating flow controller 340 via tube 322, and gas from gas reservoir 330 to reciprocating flow controller 340 via tube 332. Reciprocating flow controller 340 sends liquid to first side 352 of appliance 350 via tube 342, and gas to first side 352 of appliance 350 via tube 346. Entrained fluid is created in appliance 350. The entrained fluid pulses are used to clean the teeth and gingival area from first side 352 of appliance 350. The entrained fluid separates into gas and liquid phases.
2. Reciprocating flow controller 340 is then activated to change the fluid flow from tubes 342 and 346 to tubes 344 and 348. Reciprocating flow controller 340 sends liquid to second side 354 of appliance 350 via tube 344, and gas to second side 354 of appliance 350 via tube 348. Entrained fluid pulses are used to clean the teeth and gingival area from second side 354 of appliance 350. The entrained fluid separates into gas and liquid phases.
3. To reciprocate the cleaning fluid, steps 1 and 2 are repeated as the entrained fluid pulses are used to clean the teeth and gingival area from first side 352, and then second side 354 of appliance 350, respectively.
4. The reciprocation cycle as described continues until the time required for cleaning has expired, or the desired numbers of cycles are complete.

In this embodiment, entrained fluid, once it contacts the teeth and gingival surface, disperse into the oral cavity. In other embodiment, the liquid portion of the entrained fluid may be directed via tubes back to the reservoir 320 to be reused in the current, or a future cleaning process, or directed to disposal.

As mentioned in this embodiment, entrained fluid is created in appliance 350, in other embodiments, tube 342 may intersect tube 346 prior to appliance 350, creating entrained fluid prior to appliance 350. In a similar fashion, and tube 344 may intersect tube 348 prior to appliance 350, creating entrained fluid prior to appliance 350.

Each embodiment described in FIG. 1, FIG. 2, FIG. 3, and FIG. 4 includes a reciprocating flow controller (40, 140, 240, and 340 in FIG. 1, FIG. 2, FIG. 3, FIG. 4, respectively).

Figure 5A:
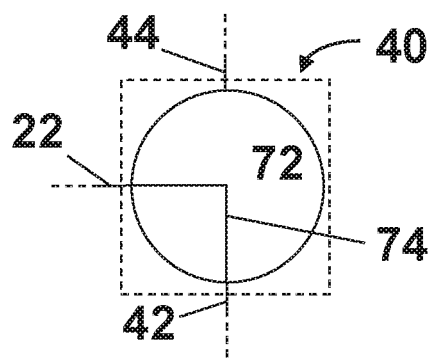
FIG. 5a is a schematic drawing of an embodiment of a reciprocating flow controller for use in a first embodiment of a system according to the present invention where the flow controller is in a first position.
Figure 5B:
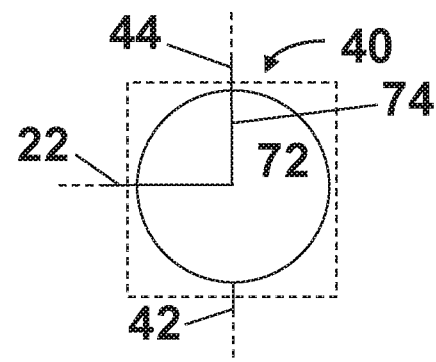
FIG. 5b is a schematic drawing of the reciprocating flow controller of FIG. 5a in a second position.

FIGS. 5a and 5b are schematic drawings of an embodiment of a reciprocating flow controller 40 used in first embodiment system according to the present invention. In FIG. 5a, reciprocating flow controller 40 is in a first position, while in FIG. 5b, reciprocating flow controller 40 is in a second position. In this embodiment, reciprocating flow controller 40 is in the form of an 1-port valve 72. An 1-port valve is a ball valve which uses a hollow, perforated and pivoting ball with L-shaped hole 74 through the ball to control flow through the valve. It is open when the ball's hole is in line with the flow and closed when it is not in line with the flow. An 1-port valve is pivoted 90-degrees to connect the center port to either side port.

In FIG. 5a, valve 72 is set so that entrained fluid from tube 22 passes through hole 74 and into tube 42. To reciprocate fluid in system 10, valve 72 is pivoted 90-degrees (as shown in FIG. 5b) so that fluid from tube 22 passes through hole 74 and into tube 44.

Figure 6A:
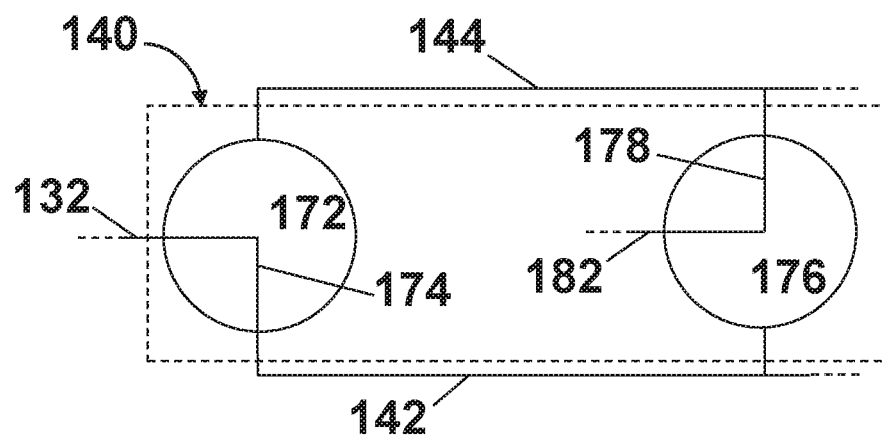
FIG. 6a is a schematic drawing of an embodiment of a reciprocating flow controller for use in a second embodiment of a system according to the present invention where the flow controller is in a first position.
Figure 6B:
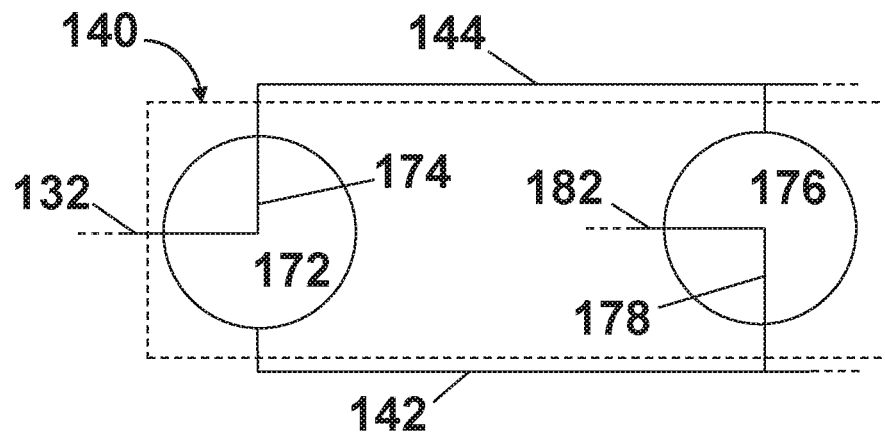
FIG. 6b is a schematic drawing of the reciprocating flow controller of FIG. 6a in a second position.

FIGS. 6a and 6b are schematic drawings of an embodiment of a reciprocating flow controller 140 used in second embodiment system according to the present invention. In FIG. 6a, reciprocating flow controller 140 is in a first position, while in FIG. 6b, reciprocating flow controller 140 is in a second position. In this embodiment, reciprocating flow controller 140 is in the form of two 1-port valves, 172 and 176. Valve 172 has L-shaped hole 174 and valve 176 has L-shaped hole 178.

In FIG. 6a, valve 172 is set so that entrained fluid from tube 132 passes through hole 174 and into tube 142. Valve 176 is set so that liquid returning from second side 154 of appliance 150 via tube 144 passes through hole 178 and into tube 182. To reciprocate fluid in system 100, valves 172 and 176 are pivoted 90-degrees (as shown in FIG. 6b) so that entrained fluid from tube 132 passes through hole 174 and into tube 144, while liquid returning from second side 154 of appliance 150 via tube 144 passes through hole 178 and into tube 182.

Figure 7A:
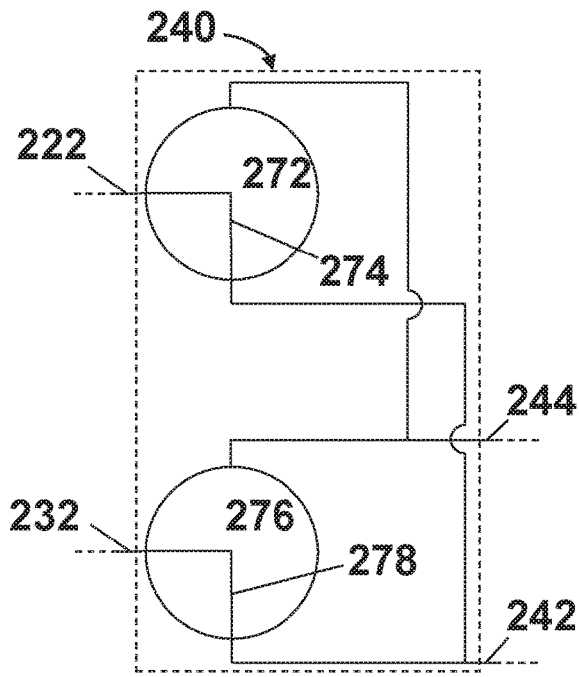
FIG. 7a is a schematic drawing of an embodiment of a reciprocating flow controller for use in a third embodiment of a system according to the present invention where the flow controller is in a first position.
Figure 7B:
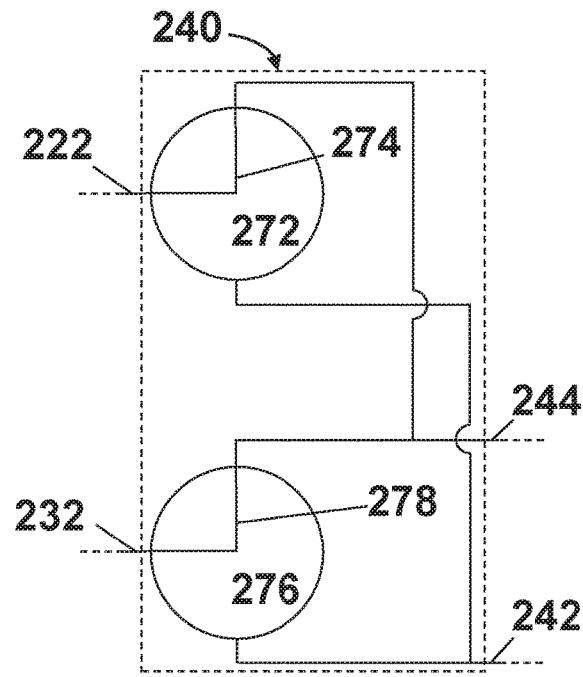
FIG. 7b is a schematic drawing of the reciprocating flow controller of FIG. 7a in a second position.

FIGS. 7a and 7b are schematic drawings of an embodiment of a reciprocating flow controller 240 used in third embodiment system according to the present invention. In FIG. 7a, reciprocating flow controller 240 is in a first position, while in FIG. 7b, reciprocating flow controller 240 is in a second position. In this embodiment, reciprocating flow controller 240 is in the form of two 1-port valves, 272 and 276. Valve 272 has L-shaped hole 274 and valve 276 has L-shaped hole 278.

In FIG. 7a, valve 276 is set so gas from tube 232 passes through hole 278 and into tube 242. Valve 272 is set so that liquid from tube 222 passes through hole 274 and intersects tube 242 at the point where entrainment occurs. As mentioned earlier, the Venturi effect may be used to entrain the liquid in the gas stream. In this embodiment, tube 242 is narrowed at one point before widening again. Liquid tube 222 is attached to the narrowed portion of tube 242, and liquid in liquid tube 222 is drawn into and entrained in gas in tube 242.

To reciprocate fluid in system 200, valves 272 and 276 are pivoted 90-degrees (as shown in FIG. 7b) so that gas from tube 232 passes through hole 274 and into tube 244. Valve 272 is set so that liquid from tube 222 passes through hole 274 and intersects tube 244 at the point where entrainment occurs. The Venturi effect may be used here to for entraining the liquid in the gas stream. Here, tube 244 is narrowed at one point before widening again. Liquid tube 222 is attached to the narrowed portion of tube 244, and liquid in liquid tube 222 is drawn into and entrained in gas in tube 244.

Figure 8A:
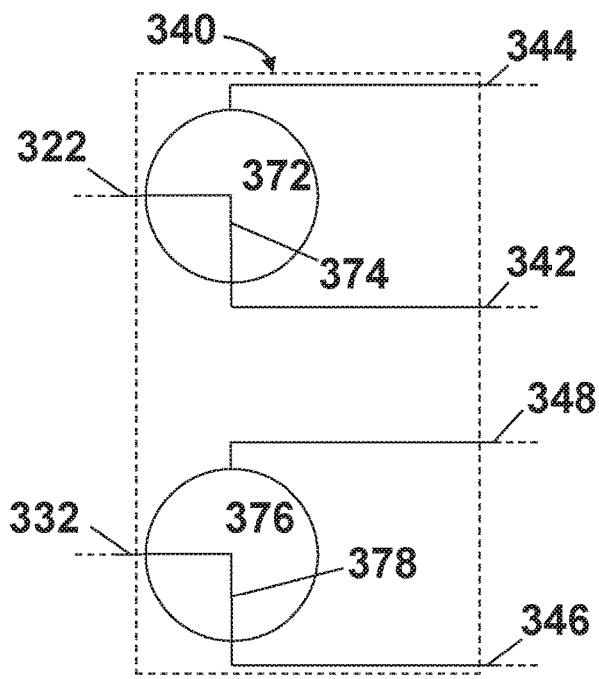
FIG. 8a is a schematic drawing of an embodiment of a reciprocating flow controller for use in a fourth embodiment of a system according to the present invention where the flow controller is in a first position.
Figure 8B:
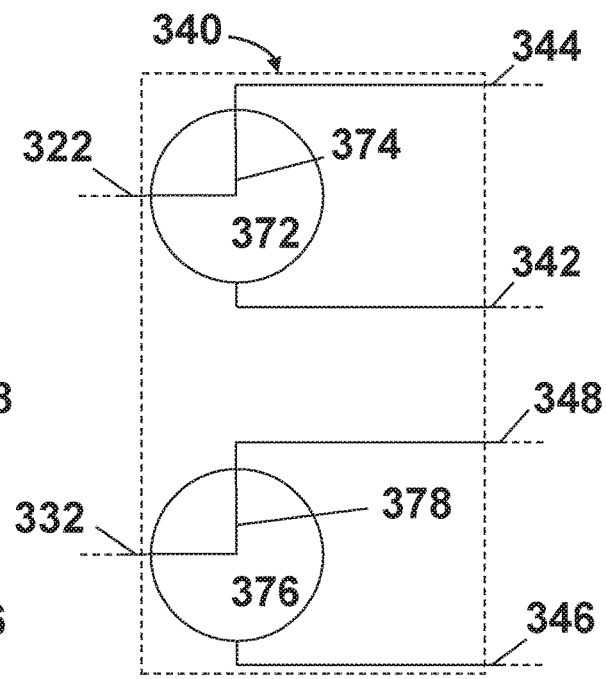
FIG. 8b is a schematic drawing of the reciprocating flow controller of FIG. 8a in a second position.

FIGS. 8a and 8b are schematic drawings of an embodiment of a reciprocating flow controller 340 used in fourth embodiment system according to the present invention. In FIG. 8a, reciprocating flow controller 340 is in a first position, while in FIG. 8b, reciprocating flow controller 340 is in a second position. In this embodiment, reciprocating flow controller 340 is in the form of two 1-port valves, 372 and 376. Valve 372 has L-shaped hole 374 and valve 376 has L-shaped hole 378.

In FIG. 8a, valve 372 is set so liquid from tube 322 passes through hole 374 and into tube 342. Valve 376 is set so that gas from tube 322 passes through hole 378 and into tube 346. To reciprocate fluid in system 300, valves 372 and 376 are pivoted 90-degrees (as shown in FIG. 8b) so that liquid from tube 322 passes through hole 374 and into tube 344. Valve 376 is set so that gas from tube 332 passes through hole 378 and into tube 348.

As mentioned earlier, appliance (50, 150, 250 or 350) may be in the form of an application tray, or mouthpiece. FIGS. 9 to 12 depict an embodiment of an application tray 1200 in which only the user's top or bottom teeth and gingival area are contacted with fluid. It should be understood that in other embodiments, application tray 1200 may be designed to substantially simultaneously contact both the top and bottom teeth and gingival area of the user, as depicted elsewhere herein.

Figure 9:
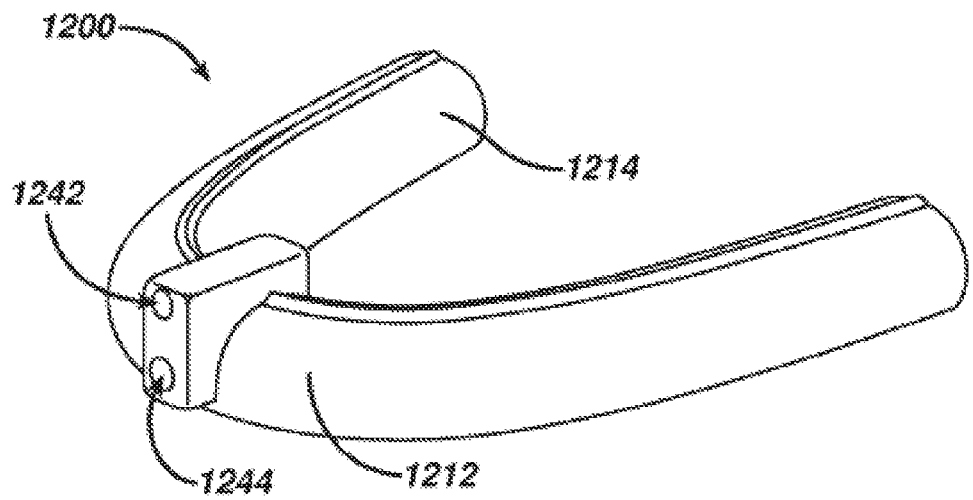
FIG. 9 is a top front perspective view of a first embodiment of an application tray for use with the present invention.
Figure 10:
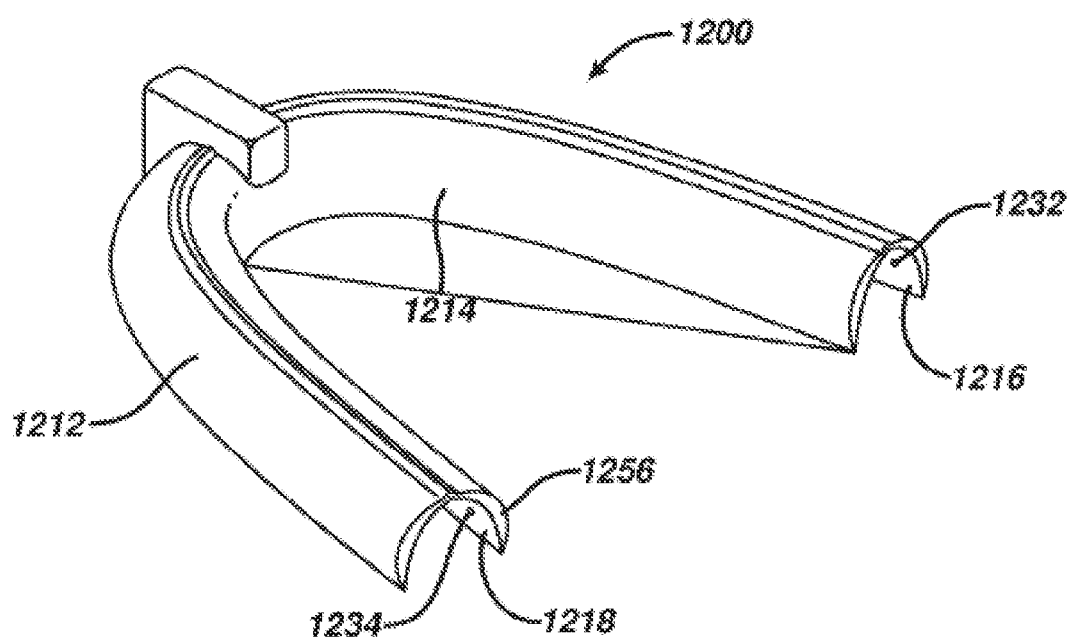
FIG. 10 is a top back view of the embodiment of the application tray of FIG. 9.
Figure 11:
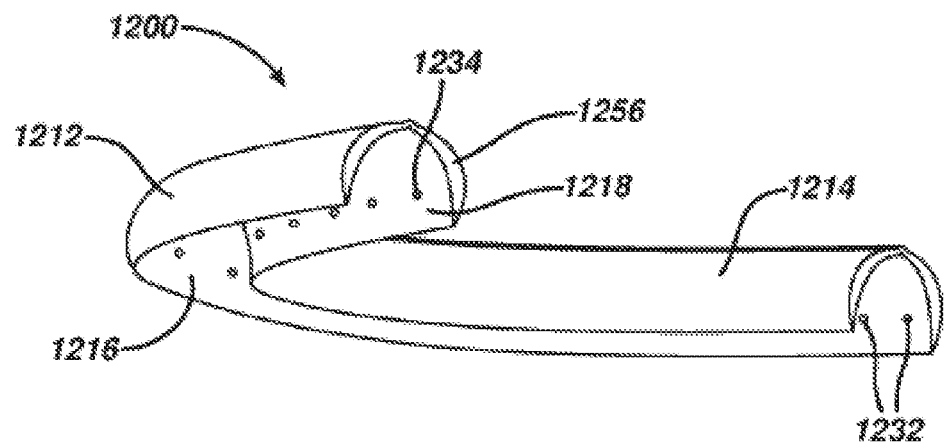
FIG. 11 is a bottom back view of the embodiment of the application tray of FIG. 9.

FIG. 9 is a top front perspective view of a application tray 1200 for use in accordance with the present invention. FIG. 10 is a top back view of the embodiment of the application tray 1200 of FIG. 9, while FIG. 11 is a bottom back view of the application tray 1200 of FIG. 9. The figures show application tray 1200 with outer front wall 1212, outer back wall 1214, inner front wall 1216, and inner back wall 1218. Inner front wall jet slots 1232 are located on inner front wall 1216, while inner back wall jet slots 1234 are located on inner back wall 1218. First port 1244 and second port 1242 enter application tray 1200 through outer front wall 1212.

The number and location of inner front wall jet slot 1232 and inner back wall jet slot 1234 as shown in FIGS. 9 to 12 is exemplary and is not intended to limit the scope of the application tray. The actual number, shape and size of inner front wall jet slots 1232 and inner back wall jet slots 1234 affect the cleaning of the teeth and gums, and can be selected or designed to direct jets of cleaning fluid in a variety of spray patterns. The inner front wall jet slots 1232 and inner back wall jet slots 1234 shown in FIGS. 9 to 11 are only one embodiment of jet slot configuration.

In other embodiments, here may also be additional wall jet slots located on outer front wall 1212, outer back wall 1214, or both walls. These jets would allow entrained fluid to be directed to the oral cavity, or the inner lips, or the tongue, to promote cleaning or treating of these areas in the mouth.

Figure 12:
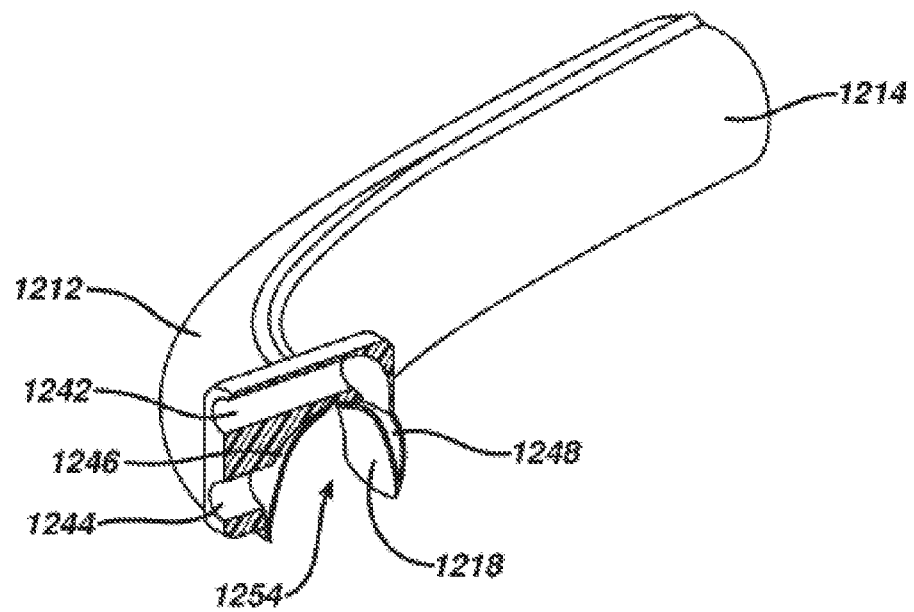
FIG. 12 is a cut-away view of the application tray of FIG. 9.

FIG. 12 is a vertical sectional view of the application tray 1200 of FIG. 9. The figures show first manifold 1246, defined as the space bordered by outer front wall 1212 and inner front wall 1216. Second manifold 1248 is defined as the space bordered by outer back wall 1214 and inner back wall 1218. The fluid contact chamber (FCC) 1254 is defined by inner front wall 1216, inner back wall 1218 and inner base wall 1250.

In one embodiment of a cleaning operation, entrained fluid enters first manifold 1246 through first port 1244 by pressure and then enters FCC 1254 through inner front wall jet slots 1232. In this embodiment, jets of entrained fluid are first directed onto the front side of the teeth, gums, and/or gingival areas. Next, the flow in the manifolds is reversed. Entrained fluid enters second manifold 1248 through second port 1242 by pressure and then enters FCC 1254 through inner back wall jet slots 1234. In the second portion of this embodiment, jets of entrained fluid are directed onto the back side of the teeth, gums, and/or gingival areas. The alternating of pressure through a number of cycles creates a turbulent, repeatable and reversible flow, thereby providing reciprocation of entrained over and about the surfaces of the oral cavity.

Figure 13:
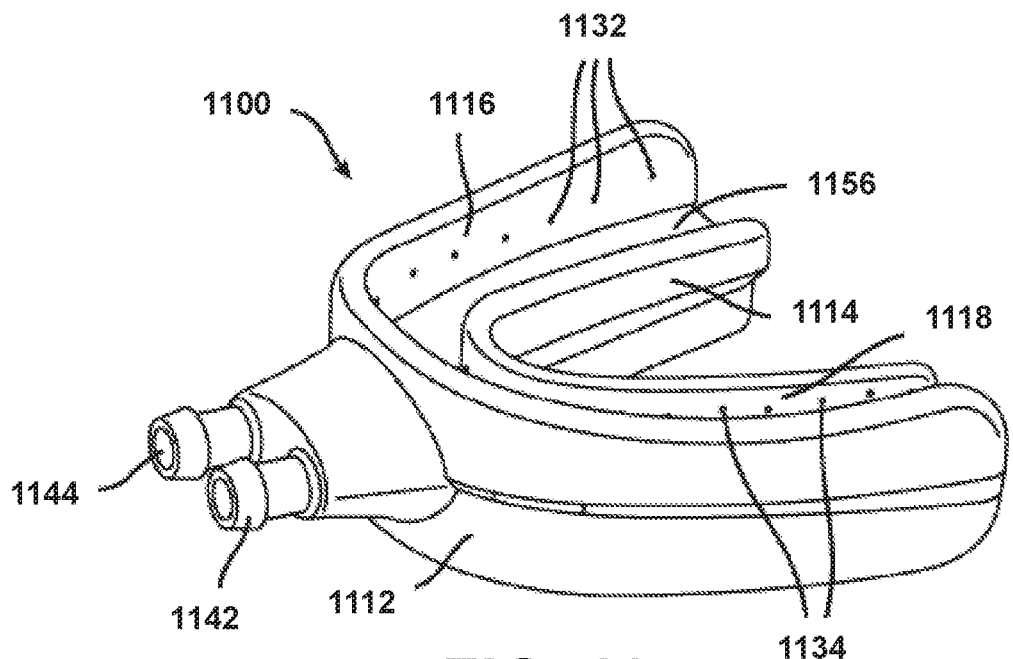
FIG. 13 is a top front perspective view of a second embodiment of an application tray for use with the present invention.
Figure 14:
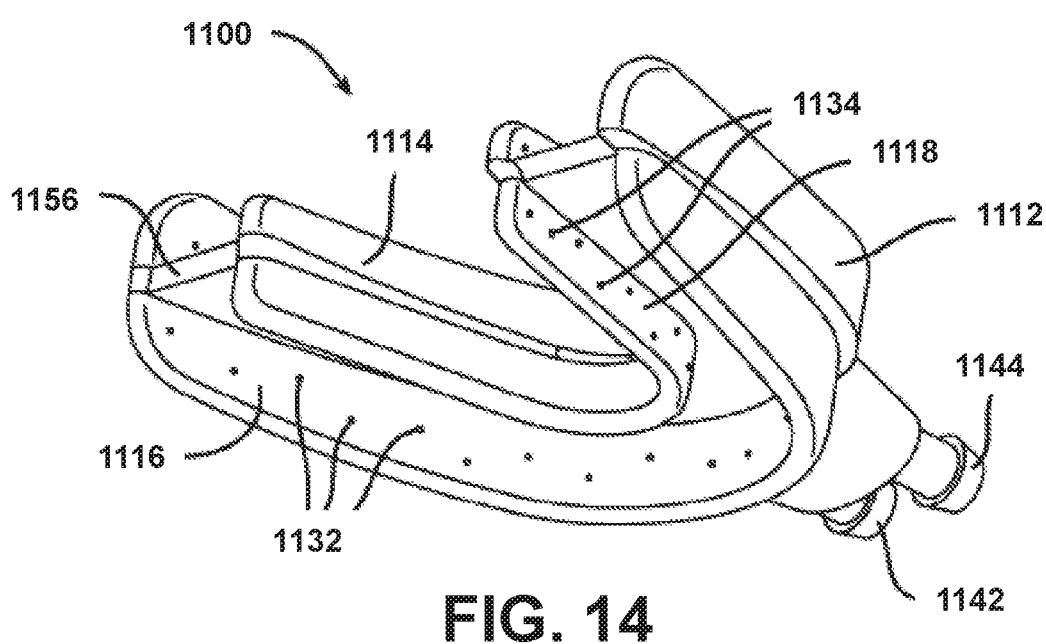
FIG. 14 is a bottom rear perspective view of the embodiment of the application tray of FIG. 13.

FIG. 13 is a top perspective view of a second embodiment of means for directing entrained fluid onto a plurality of surfaces in the oral cavity, e.g. an application tray 1100, used with devices according to the present invention. FIG. 14 is a bottom perspective view of the application tray 1100 of FIG. 13. The figures show application tray 1100 with outer front wall 1112, outer back wall 1114, inner front wall 1116, inner back wall 1118, and base membrane, e.g. bite plate, 1156. Inner front wall jet slots 1132 are located on inner front wall 1116, while inner back wall jet slots 1134 are located on inner back wall 1118. The inner front wall jet slots 1132 and inner back wall jet slots 1134 shown in FIGS. 13 and 14 are only one embodiment of jet slot configuration. First port 1142 and second port 1144 enter application tray 1100 through outer front wall 1112.

In other embodiments, here may also be additional wall jet slots located on outer front wall 1112, outer back wall 1114, or both walls. These jets would allow entrained fluid to be directed to the oral cavity, or the inner lips, or the tongue, to promote cleaning or treating of these areas in the mouth.

FIGS. 13 and 14 depict an embodiment of an application tray 1100 in which the user's top and bottom teeth and/or gingival area are substantially simultaneously contacted with fluid to provide the desired beneficial effect. It should be understood that in other embodiments, application tray 1100 may be designed to clean and/or treat only the top or bottom teeth and/or gingival area of the user.

Figure 15:
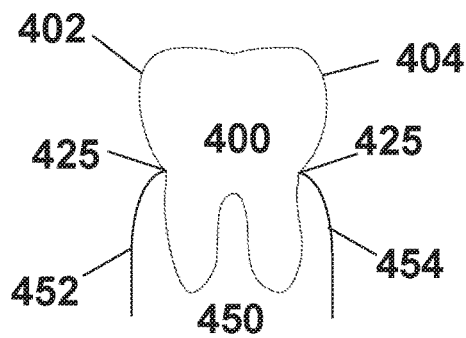
FIG. 15 is a cross-sectional view of a mammalian tooth in the gums of the oral cavity.

Entrained fluid pulses are used to clean the teeth and gingival area from either first side or second side of appliance (50, 150, 250 or 350). Appliances for use in the present invention are now discussed. FIG. 15 is a cross-sectional view of a mammalian tooth in the gums of the oral cavity. The figure shows tooth 400 with first side 402 and second side 404, as well as gum 450 with first side 452 and second side 454. Gum line 425 is at the point of intersection of tooth 400 and gum 450.

Figure 16:
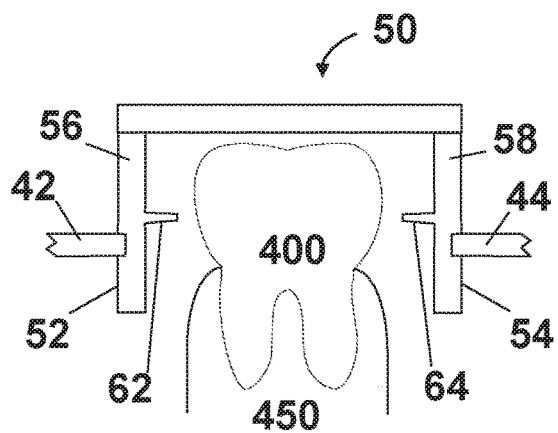
FIG. 16 is a cross-sectional view of a section of a first embodiment of an appliance used according to the present invention.

FIG. 16 is a cross-sectional view of a section of a first embodiment of an appliance 50 used according to the present invention. Appliance 50 has first side 52 and second side 54, first manifold 56 and second manifold 58, and first jet 62 and second jet 64. Tubes 42 and 44 convey entrained fluid pulses fluid to appliance 50. Tube 42 conveys fluid to the first side 52 of appliance 50, delivering the entrained fluid pulses into first manifold 56. Tube 44 conveys fluid to the second side 54 of appliance 50, delivering the entrained fluid pulses into second manifold 58. The manifolds 56, 58 deliver entrained fluid pulses to jets 62, 64, respectively. Jet 62 delivers entrained fluid pulses to with first side 402 of tooth 400, and/or first side 452 of gum 450, and/or gum line 425. Jet 64 delivers entrained fluid pulses to second side 404 of tooth 400, and or second side 454 of gum 450, and/or gum line 425. In some embodiments, delivery of entrained fluid pulses to gum line 425 is preferred. The distance from the nozzle to tooth surface is some embodiments is about 0 mm (touching the tooth surface) to about 10 mm, or about 1 mm to about 5 mm.

It should be noted that although FIG. 16 shows only one each of jets 62 and second jet 64, in some embodiments manifolds 56, 58 may deliver entrained fluid pulses to multiple jets on first side 52 and/or second side 54 of appliance 50.

In use, entrained fluid pulses would reciprocate from side to side of appliance 50. So, the cleaning operation would alternate from first side 402 to second side 404 of tooth 400, and/or first side 452 to second side 454 of gum 450. In some embodiments, during reciprocation, while first jet 62 delivers entrained fluid pulse to first side of the tooth or gum, second jet 64 simultaneously vacuums the liquid phase of the entrained fluid pulse from the second side of the tooth or gum. Then, while second jet 64 delivers entrained fluid pulse to second side of the tooth or gum, first jet 62 simultaneously vacuums the liquid phase of the entrained fluid pulse from the first side of the tooth or gum.

The description above of appliance 50 could also be used to describe appliances 150, 250, or 350. In all these embodiments, entrained fluid is created before the fluid enters the appliance. In some embodiments, entrained fluid is created after the fluid enters the appliance.

Figure 17:
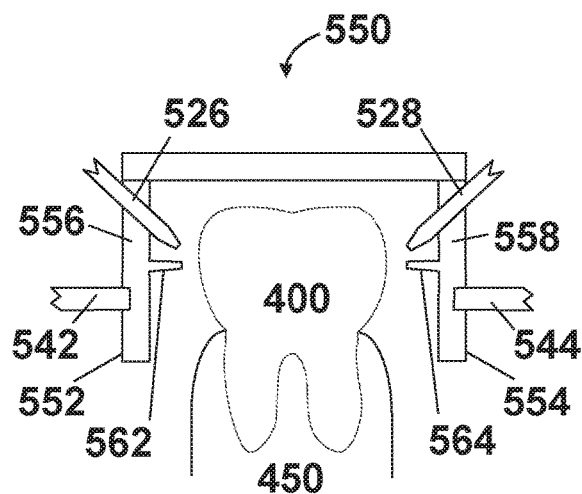
FIG. 17 is a cross-sectional view of a section of a second embodiment of an appliance used according to the present invention.

FIG. 17 is a cross-sectional view of a section of a second embodiment of an appliance 550 used according to the present invention. Appliance 550 has first side 552 and second side 554, first manifold 556 and second manifold 558, and first jet 562 and second jet 564. Tubes 542 and 544 convey liquid to appliance 550. Tube 542 conveys liquid to the first side 552 of appliance 550, delivering the liquid, which may be pulsed, into first manifold 556. Tube 544 conveys liquid to the second side 554 of appliance 550, delivering the liquid, which may be pulsed, into second manifold 558. The manifolds 556, 558 deliver liquid to jets 562, 564, respectively. Jet 562 delivers liquid to with first side 402 of tooth 400, and/or first side 452 of gum 450, and/or gum line 425. Jet 564 delivers liquid to second side 404 of tooth 400, and or second side 454 of gum 450, and/or gum line 425. In some embodiments, delivery of entrained fluid pulses to gum line 425 is preferred.

Third jet 526 delivers pulses of gas, to first side 402 of tooth 400, and/or first side 452 of gum 450, and/or gum line 425. Entrained fluid pulses are created at the intersection of the gas flow from jet 526 and the liquid flow from jet 562. Likewise, fourth jet 528 delivers pulses of gas, to second side 404 of tooth 400, and/or second side 454 of gum 450, and/or gum line 425. Entrained fluid pulses are created at the intersection of the gas flow from jet 528 and the liquid flow from jet 564.

It should be noted that although FIG. 17 shows only one each of jets 562 and second jet 564, in some embodiments manifolds 556, 558 may deliver liquid to multiple jets on first side 552 and/or second side 554 of appliance 550.

It should also be noted that third jet 526 and fourth jet 528, which both deliver gas, is preferably directed towards the surfaces being cleaned or treated.

In use, entrained fluid pulses would reciprocate from side to side of appliance 550. So, the cleaning operation would alternate from first side 402 to second side 404 of tooth 400, and/or first side 452 to second side 454 of gum 450. In some embodiments, during reciprocation, while first jet 562 delivers liquid to first side of the tooth or gum, second jet 564 simultaneously vacuums the liquid phase of the entrained fluid pulse from the second side of the tooth or gum. Then, while second jet 564 delivers liquid to second side of the tooth or gum, first jet 562 simultaneously vacuums the liquid phase of the entrained fluid pulse from the first side of the tooth or gum.

Figure 18:
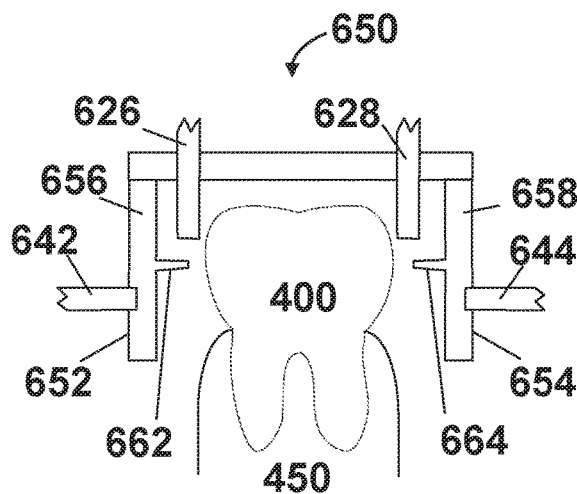
FIG. 18 is a cross-sectional view of a section of a third embodiment of an appliance used according to the present invention.

FIG. 18 is a cross-sectional view of a section of a third embodiment of an appliance 650 used according to the present invention. Appliance 650 has first side 652 and second side 654, first manifold 656 and second manifold 658, and first jet 662 and second jet 664. Tubes 642 and 644 convey gas to appliance 650. Tube 642 conveys gas to the first side 652 of appliance 650, delivering pulsed gas into first manifold 656. Tube 644 conveys gas to the second side 654 of appliance 650, delivering pulsed gas into second manifold 658. The manifolds 656, 658 deliver gas to jets 662, 664, respectively. Jet 662 delivers gas to with first side 402 of tooth 400, and/or first side 452 of gum 450, and/or gum line 425. Jet 664 delivers gas to second side 404 of tooth 400, and or second side 454 of gum 450, and/or gum line 425. In some embodiments, delivery of entrained fluid pulses to gum line 425 is preferred.

Tube 626 delivers liquid, or pulses of liquid, to first side 402 of tooth 400, and/or first side 452 of gum 450, and/or gum line 425. Entrained fluid pulses are created at the intersection of the liquid flow from tube 626 and the gas flow from jet 662. Likewise, tube 628 delivers liquid, or pulses of liquid, to second side 404 of tooth 400, and/or second side 454 of gum 450, and/or gum line 425. Entrained fluid pulses are created at the intersection of the liquid flow from tube 628 and the gas flow from jet 664.

It should be noted that although FIG. 18 shows only one each of first jet 662 and second jet 664, in some embodiments manifolds 656, 658 may deliver entrained fluid pulses to multiple jets on first side 652 and/or second side 654 of appliance 650.

It should be noted that although FIG. 18 shows tube 626 delivering liquid to the region between first jet 662 and tooth 400, in some embodiments tube 626 may deliver liquid to manifold 656. Likewise, tube 628 may deliver liquid to manifold 658. In these embodiments, entrained fluid is created in manifolds 656 and 658. Entrained fluid pulses are then delivered to tooth 400 through jets 662 and 664.

In use, entrained fluid pulses would reciprocate from side to side of appliance 650. So, the cleaning operation would alternate from first side 402 to second side 404 of tooth 400, and/or first side 452 to second side 454 of gum 450. In some embodiments, during reciprocation, while tube 626 delivers liquid to first side of the tooth or gum, tube 628 simultaneously vacuums the liquid phase of the entrained fluid pulse from the second side of the tooth or gum. Then, while tube 628 delivers liquid to the second side of the tooth or gum, tube 626 simultaneously vacuums the liquid phase of the entrained fluid pulse from the first side of the tooth or gum.

Pulsing Parameters

As noted above, in certain embodiments, the system/device of the present invention is designed to pulse one fluid (gas/liquid) into the other (liquid/gas) to create entrained fluid that is directed to at least one nozzle. In such embodiments, applicants have recognized that any of a variety of pulsing parameters may be used. In certain embodiments, the frequency of gas pulses as measured graphically (the "gas pulse frequency") that are combined with liquid/fluid pulses, is from about 0.1 Hz to about 25 Hz, including from about 0.25 Hz to about 5 Hz, including about 1 Hz. In certain embodiments, the frequency of liquid or liquid-containing fluid pulses as measured graphically (the "fluid pulse frequency") that are combined with the gas pulses, is from about 0 Hz to about 50 Hz, including from about 5 Hz to about 30 Hz, including about 25 Hz. While any suitable fluid and gas pulse frequencies may be used in accord with the present invention, applicants have discovered that in certain preferred embodiments, improved benefits can be achieved using a ratio of fluid pulse frequency to gas pulse frequency of from greater than 0 to about 50, including from greater than 0 to about 25, from greater than 0 to about 15, or from greater than 0 to about 10.

Any of a variety of other system parameters may be used. In certain embodiments, the gas is provided from its source at a gas manifold pressure of about 1 to about 100 psi, including from about 5 to about 35 psi, including from about 5 to about 20 psi, including from about 10 to about 15 psi, including about 10 psi. In certain embodiments, the gas pulse width is from about 0.100 ms to about 500 ms, including from about 5 ms to about 100 ms, including about 30 ms. In certain embodiments, the system provides a fluid pulse of about 0.0001 ml to about 1 ml per nozzle-pulse, including from about 0.001 to about 0.10 ml per nozzle-pulse.

EXAMPLES

Example 1

The system 10 as tested, and represented in FIG. 1, consists of a fluid supply reservoir 20 (Model B501, Alloy Products Corp., Waukesha, Wis.), connected by a tube 22, to a custom programmable reciprocating flow controller 40 capable of both pulsing and reciprocating fluid, liquid, or gas at frequencies 0-25 Hz with programmable pulse duty cycles of 0-100%. The controller also allowed programming of the total treatment time, the amount of time/number of pulses before reciprocating, and the number of reciprocations. The flow controller 40 conveyed the fluid to the appliance 50 though tubes 44 and/or 42 to the appliance sides 54 and/or 52, respectively. The appliance 50 for testing purposes was designed to provide a twenty nozzle array of 500-micron diameter nozzles on each side of the appliance. Nozzles were spaced evenly in a rectilinear pattern with nozzles spacing in the vertical and horizontal directions equal to 1500-micron, center to center. During testing, the nozzle exit was located in a fixed position, such that the interior nozzle would impact the target relatively perpendicular to, and at the center of, the substrate to be treated or cleaned. The interior nozzles 62 and 64 are shown in FIG. 16. The fixed distance from the nozzle exits and the biofilm covered substrate was positioned at 3000+/−500 um. Pressure was supplied to the fluid supply reservoir from a pressurized nitrogen tank (head pressure), regulated at the tank to 150 psi. Additional pressure regulation occurred post tank but before the fluid supply reservoir 20, using a pressure regulator (Model 44-2211-241, Tescom, Minneapolis, Minn.) and digital pressure indicator (60 psi, Weis, Solar Metrix, Holtsville, N.Y.). This input pressure was used to energize the fluid within the fluid supply reservoir and propel it through the system. Instrumentation and data capture and analysis software was used to measure and record the actual parameters during each test utilizing pressure sensors. The software graphed the data output of pressure vs time to allow pressure, pulse frequency, pulse width/duty cycle, reciprocation frequency and total treatment duration to be extracted from each test. This information was saved in graphical form for analysis post session (pressure vs. time graphs). Data was collected at a resolution of at least 1 KHz (i.e. one "pressure vs. time" point) every millisecond and represented and captured by a pressure graph for each session/test. The instrumentation used consisted of pressure sensors (Model MLH050PGB06A, Honeywell, Morristown, N.J.). Sensors were positioned in tubes 44 and 42 using ¼" ID barbed Tee fittings, and located within 3 inches of each of the appliance sides, 54 and 52. The pressure transducers went to a National Instruments DAQ (Model #USB-6343, National Instruments, Austin, Tex.), which was then conveyed to a commercial laptop computer with a USB-3.0 connection running National Instruments Labview and customized program to both record and display the data. AEFP occurs when the fluid supply reservoir is filled with liquid to a level that allows AEFP, where gas and liquid are simultaneously mixed and evacuated from the reservoir and supplied to the flow controller, typically <200 ml liquid. Note: All "tubes" as described above are ¼" ID×12" to 18" in length, and rated at a minimum of 150 psi pressure rating. One way valves with cracking pressures of less than 2 psi were optionally placed in tubes 22, 44, and 42 to prevent backflow.

The flow controller also allows for a second optional input/output not shown, which was used for these experiments to provide a negative differential pressure via a vacuum pump (not shown) in the appliance side/nozzles opposite the AEFP delivery. This negative pressure was created via peristaltic pump (Model #74203-47, Cole Parmer, Vernon Hills, Ill.) for all experiments where negative pressure was used. The collected fluid was discarded and not reused.

A series of trials were run with pressurized liquid (di-H2O) in fluid supply reservoir 20 to create a controlled full fluid pulse to allow control of pressure, pulse frequency, pulse width, pulse velocity and fluid reciprocation. A vacuum was applied to the side of applicator nozzles not receiving the pulse to prevent fluid accumulation at the specimen. The setup conditions utilized for the experiment are listed below:

Head Pressure: 36 psi
Appliance Manifold Pressure: 15 psi
Frequency: 25 Hz
Pulse width: 30 ms
Applicator—Rigid 20 nozzle (×2) Distance: 3 mm
Reciprocation: 15 s×2
Calculated average liquid/nozzle-pulse: 55 microliter/nozzle-pulse
Calculated average pulse velocity: 10+/−2 m/s
(Note: The reciprocation unit is defined as the amount of time the fluid is pulsed in one direction by the number of directions. So, 15 s×2 signifies that the unit pulsed for 15 seconds in the first direction and then 15 seconds in the second direction for a total of 30 seconds of treatment.)

Biofilms were grown in vivo for 7-days on 3-mm human enamel chips affixed in a denture on the buccal side in human subjects. This was done to achieve representative human biofilm characteristics experienced in the human dentitia with significant biofilm adhesion and cohesion tenacity. After 7 days growth, the enamel chips with the biofilm were removed and placed in a tooth shaped testing fixture to be representative of the surrounding tooth geometry. In this example, seven enamel chips were used.

REVEAL 100-7940 red stain (Henry Schein, Inc., Melville, N.Y.) was utilized to stain the biofilm following the instructed red dye staining procedure both before and after treatment. Post-treatment reduction in the biofilm thickness, also referred to as volumetric removal, can be determined by a reduction in the red dye signal intensity when compared to the pre-treated stained sample. This type of reduction as evidenced by the residual stain intensity on the specimen, and can range from light pink, indicating significant biofilm thickness reduction, to a bright red signaling little to no biofilm thickness reduction. The observed volumetric removal occurs due to cohesion failure within the biofilm, but maintains attachment to the specimen surface, or "cratering" in which the plaque is pushed away outward from a treated region representing by a crater like formation within the specimen. Adhesion failure, also referred to as binary removal, can be determined by the lack of stain on the post-stained specimen, resulting in predominantly white/whitish-grey visible areas on the specimen.

The cleaning rating was determined based on a scale of "poor to best". "Poor" represented no binary biofilm removal and only minor volumetric removal. "Best" represented completed binary removal from the specimen. In between the "poor to best" categories were "fair", "good", and "better" assessments. All were categorized through visual assessment of both volumetric and binary removal.

The visual cleaning ratings for the seven chips used in this test were considered to be either "poor" or "fair".

Another trial was run with pressurized liquid (di-H2O) in fluid supply reservoir 20 to create a controlled full fluid pulse to allow control of pressure, pulse frequency, pulse width, pulse velocity and fluid reciprocation. Vacuum was applied to the side of applicator nozzles not receiving the pulse. The setup conditions utilized for the experiment are listed below:

Head Pressure: 55 psi
Appliance manifold pressure: 23 psi
Frequency: 25 Hz
Pulse width: 30 ms
Applicator—Rigid 20 nozzle (×2) Distance: 3 mm
Reciprocation: 5 s×4
Calculated average liquid/nozzle-pulse: 120 microliter/nozzle-pulse
Calculated average pulse velocity: 21 m/s (Note: The reciprocation unit is defined as the amount of time the fluid is pulsed in one direction by the number of directions. So, 5 s×4 signifies that the unit pulsed for 5 seconds in the first direction and then 5 seconds in the second direction, then repeated the first and second pulsing for a total of 20 seconds of treatment.)

In-vitro biofilms, 48 hour S-mutans, were grown on a 5 mm sintered enamel like HA disk, and then placed in a tooth shaped testing fixture to provide representative oral geometry surrounding the specimen.

Again, REVEAL 100-7940 red stain (Henry Schein, Inc., Melville, N.Y.) was utilized to stain the biofilm following the instructed red dye staining procedure both before and after treatment, and the cleaning rating was determined based on the "poor to best" scale described above.

The visual cleaning rating for the chip used in this test was considered to be "fair". In this test, the fluid head pressure was increased by 50% from the process condition in the first (36 psi to 55 psi), resulting in a calculated average pulse velocity (21 m/s vs 10 m/s), two times greater than that of the earlier test. Small amounts of adhesion failure were observed within the direct impact area of the jets.

Finally, a negative control trial was run with pressurized gas (Nitrogen) in fluid supply reservoir 20 to create a controlled gas pulse to allow control of pressure, pulse frequency, pulse width, and treatment duration. Vacuum was applied to the side of applicator nozzles not receiving the pulse. The setup conditions utilized for the experiment are listed below:

Gas Input Pressure: 36 psi
Measured appliance manifold pressure: 23 psi
Pulse Frequency: 25 Hz
Pulse width: 30 ms
Applicator—Rigid 20 nozzle (×2) Distance: 3 mm (Note: the measured pressure in the appliance manifold was recorded to start at 28 psi, then gradually decrease due to the system dynamic of pressure recovery time to 14 psi at the end of 10 seconds.)

In-vitro biofilms, 48 hour S-mutans, were grown on a 5 mm sintered enamel like HA disk, and then placed in a tooth shaped testing fixture to provide representative oral geometry surrounding the specimen.

REVEAL 100-7940 red stain (Henry Schein, Inc., Melville, N.Y.) was once again utilized to stain the biofilm following the instructed red dye staining procedure both before and after treatment, and the cleaning rating was determined based on the "poor to best" scale described above.

The visual cleaning rating for the chip used in this test was considered to be "poor". This indicated that the gas alone, even at high pressures, was insufficient to cause significant biofilm disruption and removal.

Example 2

The system 100 as tested, and represented in FIG. 2, consists of a liquid supply reservoir 120 (Model B501, Alloy Products Corp., Waukesha, Wis.), and a gas supply reservoir 130. The liquid reservoir 120 supplies the liquid to tube 122, while the gas reservoir 130 supplies the gas to tube 132 which combine at the intersection of tubes 122 and 132 to create an air entrained fluid. The fluid (combined liquid and gas) is then conducted through the tube 132 to the first input of the custom programmable reciprocating flow controller 140 capable of both pulsing and reciprocating the fluid at frequencies 0-25 Hz with programmable pulse duty cycles of 0-100%. The controller also allowed programming of the total treatment time, the amount of time/number of pulses before reciprocating, and the number of reciprocations. The flow controller also allows for a second optional input/output through tube 146, which for these experiments, was used a negative differential pressure (versus the positive pressure supplied through input tube 122 via vacuum pump 180. This negative pressure was created via peristaltic pump (Model #74203-47, Cole Parmer, Vernon Hills, Ill.) for all experiments where negative pressure was used. The flow controller 140 conveys the fluid to the appliance 150 though tubes 144 or 142, and from the appliance 150 through tubes 144 or 142. In essence a four way valve, where the fluid controller 140 input at tube 122 is fluidly connected to output at tube 142, when output tube 182 is fluidly connected to tube 144. Or, where the fluid controller 140 input at tube 122 is fluidly connected to tube 144, when output tube 182 is fluidly connected to tube 142. Mostly liquid would be pulled back through tube 182 through the pump/vacuum source 180, through tube 184, where it could be collected in a separate reservoir or discarded (not shown), or captured back into the liquid reservoir 120 as show.

The appliance 150 for testing purposes was designed to provide a twenty nozzle array of 500-micron diameter nozzles on each side of the appliance. Nozzles were spaced evenly in a rectilinear pattern with nozzles spacing in the vertical and horizontal directions equal to 1500-micron, center to center. During testing, the nozzle exit was located in a fixed position, such that the interior nozzle would impact the target relatively perpendicular to, and at the center of, the substrate to be treated or cleaned. The fixed distance from the nozzle exits and the biofilm covered substrate was positioned at 3000+/−500 um. Positive Pressure was supplied to the liquid supply reservoir 120 from a pressurized nitrogen tank (head pressure), regulated at the tank to 150 psi. Additional pressure regulation occurred post tank but before the fluid supply reservoir 120, using a pressure regulator (Model 44-2211-241, Tescom, Minneapolis, Minn.) and digital pressure indicator (60 psi, Weis, Solar Metrix, Holtsville, N.Y.). This input pressure was used to energize the liquid within the fluid supply reservoir and propel it through tube 122. The gas reservoir 130 pressure was provided by an air tank, regulated to 150 psi. Additional pressure regulation occurred post air tank but before the gas reservoir 130, using a pressure regulator (Model 44-2211-241, Tescom, Minneapolis, Minn.) and digital pressure indicator (60 psi, Weis, Solar Metrix, Holtsville, N.Y.). This input pressure was used to energize the gas within the gas supply reservoir and propel it through tube 132 and then combine it in tube 132 with liquid from tube 122 to create the air entrained fluid. This was then input under positive pressure to the flow controller 140. Liquid entrained flow rate was controlled by adjusting the head gas pressure using the specified regulator and optionally further controlled using mechanical flow rate control orifices (not shown) in tube 122. Gas flow rate was controlled via the gas control regulator.

Instrumentation and data capture and analysis software was used to measure and record the actual parameters during each test utilizing pressure sensors. The software graphed the data output of pressure versus time to allow pressure, pulse frequency, pulse width/duty cycle, reciprocation frequency and total treatment duration to be extracted from each test. This information was saved in graphical form for analysis post session (pressure versus time graphs). Data was collected at a resolution of at least 1 KHz sampling rate (i.e. one "pressure versus time" point) every millisecond and represented and captured by a pressure graph for each session/test. The instrumentation used consisted of pressure sensors (Model MLH050PGB06A, Honeywell, Morristown, N.J.). Sensors were positioned in tubes 144 and 142 using ¼" ID barbed Tee fittings, and located within 3 inches of each of the appliance sides, 154 and 152. The pressure transducers data was collected through a National Instruments DAQ (Model #USB-6343, National Instruments, Austin, Tex.), which was then conveyed to a commercial laptop computer with a USB-3.0 connection running National Instruments Labview and customized program to both record and display the data. Note: All "tubes" as described above are ¼" ID×12 to 18" length, and rated at a minimum pressure rating of 150 psi.

One way valves with cracking pressures of approximately 1 psi were optionally placed in tubes 122 and 132 to prevent backflow.

Example 3

The system 200 as tested, and represented in FIG. 3, consists of a liquid supply reservoir 220 (Model B501, Alloy Products Corp., Waukesha, Wis.), a gas supply reservoir 230 (compressed air tank), a custom reciprocating flow controller 240 and custom appliance 250. The reciprocating fluid controller consisted of both custom-built and commercially available components that allow programming of both the pulse and direction (reciprocation) of flow for the both gas pulse and the liquid pulse, as well as allowing synchronous or asynchronous operation between the gas pulse and fluid pulse. This was accomplished by triggering the liquid pulse to occur at the start of the gas pulse (NI DAQ model #USB-6363, National Instruments, Austin, Tex.) connected to pressure sensors (Model MLH050PGB06A, Honeywell, Morristown, N.J.). The liquid pulse width, frequency, and direction were controlled through Labview custom program that actuated the appropriate solenoid valve (Model 71215SN2MN00N0C111P3, Honeywell, Morristown, N.J.) to control the pulsing direction and timing versus the gas pulse. The gas pulse width, frequency and direction were controlled via the custom rotary valve that is programmed and controlled through the Maxon EPOS software. For the experiments conducted, the liquid was pulsed or entrained into the gas pulse downstream of the gas pulse control, creating the air entrained fluid pulse (AEFP). The AEFP travels through tubes 244 and/or 242, depending on the programmed direction of flow and into the appliance 250. Note in another embodiment, the liquid and gas programmable controllers representing the reciprocating fluid controller 240, can be reversed. In the reversed embodiment, the gas is supplied through the solenoid/Labview controlled section of the reciprocating fluid controller 240, and the liquid was supplied through the custom rotary valve.

The reciprocating fluid controller is capable of pulsing both the liquid and the gas at frequencies of 0 to 25 Hz with programmable pulse duty cycles of 0-100% for both gas and liquid. The controller also allowed programming of the total treatment time, the amount of time/number of pulses before reciprocating, and the number of reciprocations. The flow controller also allows for a second optional input/output (not shown), which for these experiments, and connected to a vacuum pump (not shown) to create a negative differential pressure. This negative pressure was created via peristaltic pump (Model #74203-47, Cole Parmer, Vernon Hills, Ill.) for all experiments where negative pressure was used. The collected fluid was discarded and not reused.

The appliance 250 for testing purposes was designed to provide a twenty nozzle array of 500-micron diameter nozzles on each side of the appliance. Nozzles were spaced evenly in a rectilinear pattern with nozzles spacing in the vertical and horizontal directions equal to 1500-micron, center to center. During testing, the nozzle exit was located in a fixed position such that the interior nozzle would impact the target relatively perpendicular to, and at the center of, the substrate to be treated or cleaned. The fixed distance from the nozzle exits and the biofilm covered substrate was positioned at 3000+/−500 um. Positive Pressure was supplied to the liquid supply reservoir 220 from a pressurized nitrogen tank (head pressure), regulated at the tank to 150 psi. Additional pressure regulation occurred post tank but before the fluid supply reservoir 220, using a pressure regulator (Model 44-2211-241, Tescom, Minneapolis, Minn.) and digital pressure indicator (60 psi, Weis, Solar Metrix, Holtsville, N.Y.). This input pressure was used to energize the liquid within the fluid supply reservoir and propel it through tube 222. The gas reservoir 230 pressure was provided by an air tank, regulated to 150 psi. Additional pressure regulation occurred post air tank but before the gas reservoir 230, using a pressure regulator (Model 44-2211-241, Tescom, Minneapolis, Minn.) and digital pressure indicator (60 psi, Weis, Solar Metrix, Holtsville, N.Y.). This input pressure was used to energize the gas within the gas supply reservoir and propel it through tube 232 to the fluid controller. Pressurized liquid is supplied from the liquid supply reservoir 220 through tube 222 to the fluid controller. The liquid and gas are controlled, directed by their respective control systems and then combined to create the AEFP. Liquid entrained flow rate was controlled by adjusting the head gas pressure using the specified regulator and optionally further controlled using mechanical flow rate control orifices just before entrainment into the gas to create air entrained fluid. Gas flow rate was controlled via the gas control regulator.

The energized pulse flows through tubes 242 and/or 244 to the appliance. Instrumentation and data capture and analysis software was used to measure and record the actual parameters during each test utilizing pressure sensors. The software graphed the data output of pressure versus time to allow pressure, pulse frequency, pulse width/duty cycle, reciprocation frequency and total treatment duration to be extracted from each test. This information was saved in graphical form for analysis post session (pressure versus time graphs). Data was collected at a resolution of at least 1 KHz sampling rate (i.e. one "pressure vs. time" point) every millisecond and represented and captured by a pressure graph for each session/test. The instrumentation used consisted of pressure sensors (Model MLH050PGB06A, Honeywell, Morristown, N.J.). Sensors were positioned in tubes 244 and 242 using ¼" ID barbed Tee fittings, and located within 3 inches of each of the appliance sides, 254 and 252. The pressure transducers data was collected through a National Instruments DAQ (Model #USB-6363, National Instruments, Austin, Tex.), which was then conveyed to a commercial laptop computer with a USB-3.0 connection running National Instruments Labview and customized program to both record and display the data. Note: All "tubes" as described above are ¼" ID×12 to 18" length, and rated at a minimum pressure rating of 150 psi.

One way valves with cracking pressures of approximately 1 psi were optionally placed in tubes 252 and 244, to prevent backflow. The negative pressure was applied to the appliance side, 252 or 254, of the appliance 250 that was not receiving the AEFP pulse.

A series of trials were run with liquid (di-H2O) in fluid supply reservoir 220 and nitrogen gas in supply reservoir 230 to create a controlled entrained fluid pulse (AEFP), allowing control of the fluid entrainment rate, gas pulse pressure, pulse frequency, pulse width, and fluid reciprocation. A vacuum was applied to the side of applicator nozzles not receiving the pulse to prevent fluid accumulation at the specimen. The setup conditions utilized for the experiment are listed below:

Head Pressure: 10 psi
Appliance Manifold Pressure: 8 psi
Frequency: 25 Hz
Pulse width: 30 ms
Applicator—Rigid 20 nozzle (×2) Distance: 3 mm
Reciprocation: 15 s×2
Calculated average liquid/nozzle-pulse: 40 microliter/nozzle-pulse
Approximate liquid pulse velocity (HSVM): 10+/−2 m/s
(Note: Velocity was measured post testing via pixel tracking using High Speed Video Microscope, or HSVM).

In operation, 160 ml of liquid was entrained at a constant rate for first 8 seconds of operation in each direction. The remaining 7 seconds in each direction was primarily pulsed gas only.

Biofilms were grown in vivo for 7-days on 3-mm human enamel chips affixed in a denture on the buccal side in human subjects. This was done to achieve representative human biofilm characteristics experienced in the human dentitia with significant biofilm adhesion and cohesion tenacity. After 7 days growth, the enamel chips with the biofilm were removed and placed in a tooth shaped testing fixture to be representative of the surrounding tooth geometry. In this example, twelve enamel chips were used.

REVEAL 100-7940 red stain (Henry Schein, Inc., Melville, N.Y.) was utilized to stain the biofilm following the instructed red dye staining procedure both before and after treatment. Post-treatment reduction in the biofilm thickness, also referred to as volumetric removal, can be determined by a reduction in the red dye signal intensity when compared to the pre-treated stained sample. This type of reduction as evidenced by the residual stain intensity on the specimen, and can range from light pink, indicating significant biofilm thickness reduction, to a bright red signaling little to no biofilm thickness reduction. The observed volumetric removal occurs due to cohesion failure within the biofilm, but maintains attachment to the specimen surface, or "cratering" in which the plaque is pushed away outward from a treated region representing by a crater like formation within the specimen. Adhesion failure, also referred to as binary removal, can be determined by the lack of stain on the post-stained specimen, resulting in predominantly white/whitish-grey visible areas on the specimen.

The cleaning rating was determined based on a scale of "poor to best". "Poor" represented no binary biofilm removal and only minor volumetric removal. "Best" represented completed binary removal from the specimen. In between the "poor to best" categories were "fair", "good", and "better" assessments. All were categorized through visual assessment of both volumetric and binary removal.

The visual cleaning rating for the twelve chips used in this test was considered to be "good/better". In this test, with the addition of the gas pulse input, and entraining liquid at a constant rate, the gas input pressure and liquid head pressure was decreased by more than two/thirds from the process conditions in Example 1 (55/36 psi down to 10 psi), with measured peak liquid particle velocities in the range of 10+/−2 m/s. The in-situ grown saliva biofilm disruption and removal results were significantly improved when compared to the two tests from Example 1.

Another series of trials were run with liquid formulation (di-H20 w/10% silica Tixosil 63:Dioxyde de silicium, $SiO_2$) in fluid supply reservoir 220 and nitrogen gas in supply reservoir 230 to create a controlled entrained fluid pulse (AEFP), allowing control of the fluid entrainment rate, gas pulse pressure, pulse frequency, pulse width, and fluid reciprocation. A vacuum was applied to the side of applicator nozzles not receiving the pulse to prevent fluid accumulation at the specimen. The $SiO_2$ was provided as an abrasive in the formulation. The setup conditions utilized for the experiment are listed below:

Head Pressure: 10 psi
Appliance Manifold Pressure: 7 psi
Frequency: 25 Hz
Pulse width: 30 ms
Applicator—Rigid 20 nozzle (×2) Distance: 3 mm
Reciprocation: 15 s×2
Calculated average liquid/nozzle-pulse: 35 microliter/nozzle-pulse
Approximate liquid pulse velocity (HSVM): 10+/−2 m/s
(Note: Velocity was measured post testing via pixel tracking using High Speed Video Microscope, or HSVM).

In operation, 160 ml of liquid was entrained at a constant rate for first 9 seconds of operation in each direction. The remaining 6 seconds in each direction was primarily pulsed gas only.

Biofilms were grown in vivo for 7-days on 3-mm human enamel chips affixed in a denture on the buccal side in human subjects as discussed earlier in this example. Also, REVEAL 100-7940 red stain (Henry Schein, Inc., Melville, N.Y.) was utilized to stain the biofilm as discussed earlier, and the cleaning rating was determined based on a scale of "poor to best".

The visual cleaning rating for the ten chips used in this test was considered to be "better/best". In this test, an abrasive was added to the formulation. The abrasive improved the overall cleaning results when compared to all previous tests.

Still another series of trials were run with liquid (di-H2O) in fluid supply reservoir 220 and nitrogen gas in supply reservoir 230 to create a controlled entrained fluid pulse (AEFP), allowing control of the fluid entrainment rate and pulse frequency, gas pulse frequency, and pulse width. Fluid reciprocation was not utilized. A vacuum was applied to the side of applicator nozzles not receiving the pulse to prevent fluid accumulation at the specimen. The setup conditions utilized for the experiment are listed below:
Gas Head Pressure: 20 psi
Liquid head Source Pressure: 10 psi
Pulse width: 30 ms
Applicator—Rigid 20 nozzle (×2) Distance: 3 mm
Calculated average liquid/nozzle-pulse: 40 ul+/−15 ul per nozzle-pulse In this set of trials, the liquid pulse frequency and the gas pulse frequency were varied, and the liquid to gas pulse frequency ratios were calculated. The liquid pulse frequency ranged from 0 HZ (no liquid supplied) to 25 HZ, and the gas pulse frequency ranged from 0.5 HZ to 25 HZ. In one trial, liquid was supplied at a constant rate, and the gas pulse frequency was 25 HZ. The time of treatment was also varied, and the total gas pulses were calculated and reported for each test.

In-vitro biofilms, 48 hour S-mutans, were grown on a 5 mm sintered enamel like HA disk, and then placed in a tooth shaped testing fixture to provide representative oral geometry surrounding the specimen.

Again, REVEAL 100-7940 red stain (Henry Schein, Inc., Melville, N.Y.) was utilized to stain the biofilm following the instructed red dye staining procedure both before and after treatment. Following the post treatment and digital imaging of the red stained sample, the specimens were then stained with a crystal violet stain (Harleco (EMD Chemicals), 65092A-95) to provide improved contrast for visual image analysis. The cleaning rating was determined based on the "poor to best" scale described in all previous examples.

Table 1 shows the effect of liquid to gas pulse frequency ratio to observed cleaning.

TABLE 1

Cleaning performance versus liquid to gas pulse frequency ratio.

| Trial no. | Fluid pulse frequency (Hz) | Gas pulse frequency (Hz) | Fluid/Gas frequency ratio | Cleaning time (s) | Total number of gas pulses | Cleaning rating |
|---|---|---|---|---|---|---|
| 5* | Constant | 25 | — | 15 | 375 | Best |
| 6 | 1 | 10 | 0.1 | 30 | 300 | Best |
| 7 | 25 | 20 | 1.3 | 15 | 300 | Best |
| 8 | 25 | 10 | 2.5 | 30 | 300 | Best |
| 9 | 5 | 1.5 | 3.3 | 120 | 180 | Best |
| 10 | 25 | 5 | 5 | 30 | 150 | Best |
| 11 | 5 | 0.5 | 10 | 30 | 15 | Better |
| 12 | 25 | 2 | 12.5 | 30 | 60 | Good |
| 13 | 10 | 0.5 | 20 | 30 | 15 | Fair |
| 14 | 25 | 0.5 | 50 | 30 | 15 | Fair |
| 15** | 0 | 25 | 0 | 10 | 250 | Poor |

*No gas flow.
**No liquid flow.

Table 1 shows that there was a correlation between the Fluid/Gas pulse frequency ratio and the cleaning rating. When the fluid pulse/gas pulse ratio was below 10, the visual cleaning rating was "better" to "best" (translating to approximately 100% biofilm removal). Ratios above 10 provided "good" to "fair" results. So, a higher the gas pulse frequency (versus pulse frequency), the more improved the disruption and removal of the biofilm from the specimen.

Example 4

The system 300 as tested, and represented in FIG. 4, consists of a liquid supply reservoir 320 (Model B501, Alloy Products Corp., Waukesha, Wis.), a gas supply reservoir 330 (compressed air tank), a custom reciprocating flow controller 240 and custom appliance 350. The reciprocating fluid controller consisted of both custom-designed/built and commercially available components that allow programming of both the pulse and direction (reciprocation) of flow for the both gas pulse and the liquid pulse, as well as allowing synchronous or asynchronous operation between the gas pulse and fluid pulse. This was accomplished by triggering the liquid pulse to occur at the start of the gas pulse (NI DAQ model #USB-6363, National Instruments, Austin, Tex.) connected to pressure sensors, Model MLH050PGB06A, Honeywell, Morristown, N.J.). The liquid pulse width, frequency, and direction were controlled through Labview custom program that actuated the appropriate solenoid valve (Model 71215SN2MN00N0C111P3, Honeywell, Morristown, N.J.) to control the pulsing direction and timing of the liquid pulse through tubes 342 and/or 344. The gas pulse width, frequency and direction were controlled via the custom rotary valve that is programmed and controlled through the Maxon EPOS software. The gas pulse was delivered to the tubes 346 or 348, depending on the reciprocation direction and the liquid pulse direction, such that if liquid pulse was being delivered to first side 352, from tube 342, then gas pulse was also delivered to the first side 352 from tube 346. Conversely, if the liquid pulse was second side 354 from tube 344, then the gas pulse would also be delivered to the second side 354, through tube 348. Also, gas and liquid could be supplied to both first side 352 and second side 354, through tubes 342, 346, 344, and 348 respectively. For the purpose of these experiments, gas and liquid were supplied to the first side 352 through tubes 342 and 346, while fluid was removed from the second side 354 through tubes 344 by creating negative relative pressure using a peristaltic pump (Model #74203-47, Cole Parmer, Vernon Hills, Ill.).

The flow controller also allows for a second optional input/output (not shown), which was used for these experiments to provide a negative differential pressure via a vacuum pump (not shown) in the side opposite AEFP delivery. This negative pressure was created via the peristaltic pump for all experiments where negative pressure was used. The collected fluid was discarded and not reused. The reciprocating fluid controller is capable of pulsing at frequencies of 0 to 25 Hz with programmable pulse duty cycles of 0-100% for either gas and/or liquid. The controller also allowed programming of the total treatment time, the amount of time/number of pulses before reciprocating, and the number of reciprocations.

The appliance 350 that was used for testing purposes was designed to provide a twenty nozzle array of 500 um dia. nozzles on each side of the appliance. Nozzles were spaced evenly in a rectilinear 4×5 pattern with nozzles spacing in the vertical and horizontal directions equal to 1500-micron, center to center. During testing, the nozzle exit was located in a fixed position, such that the interior nozzle would impact the target relatively perpendicular to, and at the center of the substrate to be treated or cleaned. Nozzles 562 and 564, and 662 and 664, in FIGS. 17 and 18, respectively, illustrate the direction and position relative to the teeth 400 of these nozzles. In addition, as separate set of nozzles 526, 528, and 626 and 628, as depicted in FIGS. 17 and 18, respectively, and aligned vertically with the nozzles columns represented by nozzles 542, 544, 642, and 644. The fixed distance from the nozzle exits and the biofilm covered substrate was positioned at approximately 3000 microns. During the experimental testing, the air pulse was supplied to the teeth through nozzle array represented in FIG. 18 by nozzle 662, and the liquid was entrained into the gas pulse through nozzle array 662, to create the AEFP prior to contacting the teeth. Vacuum was applied to the opposite side during the experiments for removal of fluid through nozzle array on the opposite side, represented by nozzle 644. Conversely, fluid could be injected/entrained into the appliance chamber through nozzles 562 and/or 544 as shown in FIG. 17, with the gas pulse supplied via nozzle 526 and/or 528, to create the AEFP prior to tooth impact.

Positive Pressure was supplied to the liquid supply reservoir 320 from a pressurized nitrogen tank (head pressure), regulated at the tank to 150 psi. Additional pressure regulation occurred post tank but before the fluid supply reservoir 320 using a pressure regulator (Model 44-2211-241, Tescom, Minneapolis, Minn.) and digital pressure indicator (60 psi, Weis, Solar Metrix, Holtsville, N.Y.). This input pressure was used to energize the liquid within the fluid supply reservoir and propel it through tube 322. Gas reservoir 330 pressure was provided by an air tank, regulated to 150 psi. Additional pressure regulation occurred post air tank but before the gas reservoir 330, using a pressure regulator (Model 44-2211-241, Tescom, Minneapolis, Minn.) and digital pressure indicator (60 psi, Weis, Solar Metrix, Holtsville, N.Y.). This input pressure was used to energize the gas within the gas supply reservoir and propel it through to the fluid controller through tube 332. Pressurized liquid is supplied from the liquid supply reservoir 320 through tube 322 to the fluid controller.

Liquid entrained flow rate was controlled by adjusting the head gas pressure using the specified regulator and optionally further controlled using mechanical flow rate control orifices (not shown) in tubes 322, or 344 and 342. Gas flow rate was controlled via the gas control regulator.

The liquid and gas are controlled, directed by their respective control systems and then combined to create the AEFP, after exiting the nozzles in the appliance but before contacting the teeth. Instrumentation and data capture and analysis software was used to measure and record the actual parameters during each test utilizing pressure sensors. The software graphed the data output of pressure vs time to allow pressure, pulse frequency, pulse width/duty cycle, reciprocation frequency and total treatment duration to be extracted from each test. This information was saved in graphical form for analysis post session (pressure versus time graphs). Data was collected at a resolution of at least 1 KHz sampling rate (i.e. one "pressure vs. time" point) every millisecond and represented and captured by a pressure graph for each session/test. The instrumentation used consisted of pressure sensors (Model MLH050PGB06A, Honeywell, Morristown, N.J.). Sensors were positioned within the tubes 342, 344, 346 and 348 using ¼" ID barbed Tee fittings, and located within 3 inches of each of the appliance sides, 354 and 352. The pressure transducers data was collected through a National Instruments DAQ (Model #USB-6363, National Instruments, Austin, Tex.), which was then conveyed to a commercial laptop computer with a USB-3.0 connection running National Instruments Labview and customized program to both record and display the data. Note: All "tubes" as described above are ¼" ID×12 to 18" length, and rated at a minimum pressure rating of 150 psi.

One way valves with cracking pressures of approximately 1 psi were optionally placed in tubes 252 and 244, to prevent backflow. The negative pressure was applied to the appliance side, 252 or 254, of appliance 250 that was not receiving the AEFP pulse.

What is claimed is:

1. An oral care system configured for cleaning or treating a user's oral cavity comprising:
    a. an appliance comprising a first and second plurality of nozzles, said appliance configured to be held in the mouth of the user with said first and second plurality of nozzles in fluid communication with one or more surfaces of the user's oral cavity;
    b. a source of gas,
    c. a source of liquid; and
    d. a reciprocating fluid controller for directing fluid to said appliance;
wherein such system is configured such that gas from said source of gas is pulsed from said reciprocating fluid controller to said first plurality of nozzles in said appliance at a gas pulse frequency of from 0.1 Hz to 25 Hz and liquid from said source of liquid is pulsed into the gas pulsed from the reciprocating fluid controller at a liquid pulse frequency of greater than 0 Hz to 50 Hz by the reciprocating fluid controller, which to form entrained fluid between said reciprocating fluid controller and said first plurality of nozzles and wherein i) the liquid pulse frequency and direction and ii) the gas pulse frequency and direction are controlled by programming and the reciprocating fluid controller and further wherein the liquid pulse frequency and direction is controlled by programming different from the programming controlling the gas pulse frequency and direction, a frequency ratio (liquid/gas) is from greater than zero to 50, and said source of gas provides gas at a pressure of 5 to 20 psi and said reciprocating fluid controller reciprocating the flow of the fluid, liquid and gas.

2. The system of claim 1 wherein said frequency ratio (liquid/gas) is from greater than zero to 15.

3. The system of claim 1 wherein said frequency ratio (liquid/gas) is from greater than zero to 10.

4. The system of claim 1 wherein said source of gas provides gas at a pressure of 10 to 15 psi.

5. The system of claim 1 wherein said system provides a fluid pulse of 0.001 to 0.10 ml per nozzle-pulse.

6. A method of providing an oral care benefit to one or more surfaces of the oral cavity comprising holding an appliance of a system according to claim 1 in the mouth of a user and operating said system to direct entrained fluid to and remove fluid from said appliance.

7. The method of claim 6 wherein said entrained fluid comprises a mouthwash liquid.

8. The method of claim 7 wherein said mouthwash liquid comprises water and one or more essential oils selected from the group consisting of menthol, thymol, eucalyptol, methyl salicylate and combinations of two or more thereof.

9. The method of claim 8 wherein said mouthwash liquid comprises ethanol.

10. The method of claim 8 wherein said mouthwash liquid is free of ethanol.

11. The system of claim 1 wherein said liquid is pulsed at a frequency of from 5 to 30 Hz.

12. The system of claim 3 wherein said liquid is pulsed at a frequency of from 5 to 30 Hz.

* * * * *